United States Patent
Barbera-Guillem et al.

(10) Patent No.: US 6,251,616 B1
(45) Date of Patent: Jun. 26, 2001

(54) METHODS AND ASSAY KITS FOR DETECTING ALTERED MONONUCLEAR CELL PHENOTYPE RELATED TO A PRO-TUMOR IMMUNE RESPONSE

(75) Inventors: Emilio Barbera-Guillem, Powell; M. Bud Nelson, Worthington, both of OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/435,289

(22) Filed: Nov. 5, 1999

Related U.S. Application Data

(63) Continuation-in-part of application No. 09/333,103, filed on Jun. 15, 1999, now abandoned.
(60) Provisional application No. 60/115,946, filed on Jan. 14, 1999, and provisional application No. 60/117,895, filed on Jan. 29, 1999.

(51) Int. Cl.[7] .................. G01N 33/574; G01N 33/53; G01N 33/555; G01N 33/567
(52) U.S. Cl. .................. 435/7.24; 435/7.23; 435/975
(58) Field of Search .................. 435/7.24, 7.23, 435/975

(56) References Cited

PUBLICATIONS

Fernsten et al., Expression of the sialosyl–Tn epitope on CD45 derived from activated peripheral blood T cells, Immunological Investigations, vol. 27, pp. 323–338, 1998.
1998 Catalogue—Coulter–Immunotech, Multi–color product section, pp. 124–140.

Domagala et al., "Distribution of T Lymphocytes and B Lymphocytes in Peripheral Blood and Effusions of Patients with Cancer", 1978, J. Natl. Cancer Institute, vol. 61:295–300.
Wood and Neff, "A Reevaluation of B–Lymphocyte Levels in Peripheral Blood From Cancer Patients", 1978, J. Natl. Cancer Inst., vol. 61:715–719.
Eremin et al., "T and B Lymphocyte Populations in Human Normal Lymph Node, Regional Tumor Lymph Node and Inflammatory Lymph Nodes", Int. Archs. Allergy Appl. Immunology, vol. 52:277–290, 1976.
Svennevig et al., "Isolation and characterization of lymphocytes and macrophages from solid, malignant human tumors"; 1979, Int. J. Cancer, vol. 23:626–631.
Parwaresch et al., "Monoclonal antibody Ki–M4 specifically recognizes human dendritic reticulum cells (follicular dendritic cells) and their possible precursor in blood"; 1983, Blood, vol. 62, No. 3: 585–590.

*Primary Examiner*—Yvonne Eyler
*Assistant Examiner*—Jennifer Nichols
(74) *Attorney, Agent, or Firm*—M. Bud Nelson

(57) ABSTRACT

A method for screening for a pro-tumor immune response according to the present invention, the method comprises: contacting a clinical sample with one or more detector molecules for detecting, and then determining the amount of, mononuclear cell phenotype in the sample; and (b) comparing the amount of mononuclear cell phenotype determined in the sample to a reference value for the mononuclear cell phenotype; wherein a significant difference in the amount of mononuclear cell phenotype determined as compared to the reference value may be an indicator of the presence of a pro-tumor immune response. Also provided are assay kits for determining an amount of mononuclear cell phenotype in performing the methods according to the present invention.

8 Claims, 4 Drawing Sheets

METHODS AND ASSAY KITS FOR DETECTING ALTERED MONONUCLEAR CELL PHENOTYPE RELATED TO A PRO-TUMOR IMMUNE RESPONSE

This is application is a continuation-in-part application based on earlier nonprovisional application Ser. No. 09/333,103 filed Jun. 15, 1999 now abandoned which is a nonprovisional application based on a provisional application Ser No. 60/115,946 filed Jan. 14, 1999; and a nonprovisional application based on earlier co-pending patent application Ser. No. 60/117,895 filed Jan. 29, 1999; all of which are herein substantially incorporated by reference.

FIELD OF THE INVENTION

The present invention is related to biological testing, and in particular to methods for determining the amount of mononuclear cell phenotype comprising one or more selected subpopulations of mononuclear cells which may be associated with, or an indicator for, the progression of solid, non-lymphoid tumors. More particularly, the present invention is related to the discovery and detection of altered mononuclear cell phenotypes in lymphoid tissues and body fluids of individuals having an immune response which promotes tumor progression. Altered mononuclear cell phenotype comprises an alteration in the amount of one or more lymphocyte subpopulations, one or more follicular dendritic cell subpopulations, and a combination thereof; each subpopulation of which may be used singly or in combination with other subpopulations as a diagnostic indicator in screening for the presence of a pro-tumor immune response in humans, and as a prognostic indicator in screening for the potential of tumor development or recurrence.

BACKGROUND OF THE INVENTION

1. B cells

The response of an individual to tumor cells involves the reactions and counteractions mediated by both cellular and humoral arms of the immune system. Tumor cell growth may represent a disturbance in the equilibrium of the immune system that is pre-existing, and/or induced by the tumor cells themselves. However, most investigations to date have focused on the role of T cells in tumor immunity. The role of B cells in a tumor-bearing individual still remains unclear.

Previous studies have shown that lymph nodes regional to a primary tumor in cancer patients, and in in vivo experimental animal models of tumor development, can undergo a prominent expansion in the germinal centers (Eremin et al., 1980, Br. J. Cancer 41:62; Bertschmann et al., 1984, Br. J. Cancer 49:477–484). In lymph nodes, prominent expansion of immune cells includes B lymphocytes (B cells). The reason(s) for this observed B cell pro-liferative response remains unclear, and may be due to either activation and stimulation directly by tumor cells or tumor cell components, and/or indirectly by stimulation of T-helper cells which then activate and stimulate B cells. A recent study confirmed the increase in the number of B cells in lymph nodes regional to primary tumors (Ito et al., 1996, Immunobiol. 195:1–15). The number of B cells increase in the regional lymph nodes concomitantly with tumor development, and such B cells appear to be able to elicit anti-tumor immunity. In that regard, there are numerous reports that cancer patients have circulating antitumor antibodies (see, e.g., Carey et al., 1976, Proc. Natl. Acad. Sci. USA 73:3278–3282; Abe et al., 1989, Cancer Res. 80:271–276; Christensen et al., 1989, Int. J. Cancer 37:683–688).

However, unlike the pattern found in the lymph nodes, the percentage of B lymphocyte populations in the blood of cancer patients are similar to the values found in healthy controls (Eremin et al., 1976, Int. Archs Allergy appl. Immun. 52:277–290; Svennevig et al., 1979, Int. J. Cancer 23:626–631). Some studies report a lower mean percentage of circulating B lymphocytes in cancer patients as compared to the mean percentage in apparently normal individuals (Wood and Neff, 1978, J. Natl. Cancer Inst. 61:715–718). In these latter studies, the low values of circulating B lymphocytes were observed both in the absence of therapy, and in the presence of chemotherapy or radiation therapy; and further, could not be found to correlate with the stage of disease. More recently, the percentage of a specific subpopulation of B lymphocytes, identified as CD5+ and also known as B1 cells, appears to be slightly increased in the peripheral blood of cancer patients as compared to the values in healthy controls (Stein et al., 1991, Clin. Exp. Immunol. 85:418–23). It is noted that CD5+ B cells are a different cell subset than memory B cells (CD5–; Brown, 1992, Crit. Rev. Immunol. 11:395–417). While it appears that a humoral immune response towards tumor-associated antigens can be mounted in cancer patients, the role of the B cells in the host response to tumor, and any significance relative to the detection of B cells in the host response to tumor, remain poorly defined.

2. T cells

T cell subsets, mainly CD4+ cells and CD8+ cells, have been studied in individuals having solid, nonlymphoid tumor. In general, regional lymph nodes close to (e.g., draining) a primary solid, nonlymphoid tumor, and the nodes involved with metastases thereof, show a significant decrease of CD4+ T cells (see, e.g., Takemura et al., 1991, Cancer J. 4:244–248). As to peripheral blood values, it is a general observation that activated CD4+ T cells (CD4+ , HLA DR+) may be significantly higher in amounts in Stage I patients than that observed in healthy controls, but that the CD4+ subset becomes significantly decreased during advanced stages of malignancy. In patients with bladder cancer, the absolute number of CD11b+ CD8+ cells (suppressor T lymphocytes) in peripheral blood correlated inversely with histological grade. Additionally, there was a significantly lower absolute number of peripheral blood CD11b– CD8+ cells (cytotoxic T lymphocytes) in patients with invasive bladder cancer as compared to that in patients with superficial bladder cancer (see, e.g., Ono et al., 1996, Reg. Cancer Treat. 9:40–43). It has also been reported that radiation therapy for primary cancer results in reduced B lymphocytes and reduced T lymphocytes in proportion to their total lymphocyte population, so that their percentages remain unchanged.

3. Follicular dendritic cells

Dendritic cells are a population of antigen presenting cells that comprise multiple distinct subpopulations. The distinct subpopulations of dendritic cells include: (a) Langerhans cells found in the skin above the basal layer of proliferating keritinocytes (e.g., CD1a+); (b) interdigitating dendritic cells (CD40$^{high}$, B7.1/CD80$^{high}$, B7.2/CD86$^{high}$); and follicular dendritic cells (DRC-1, KIM4+) (see, e.g., Liu and Arpin, 1997, Immunol. Rev. 156:111–126). Follicular dendritic cells (FDC) reside in germinal centers within lymphoid follicles of secondary lymphoid tissues. FDC have a distinctive ability to trap and retain unprocessed antigen, in the form of immune complexes, in a spacial arrangement for effective antigen presentation to B cells. Hence, FDC are the main antigen presenting cells to B cells in the germinal center, and play a major role in inducing B cell proliferation in lymph nodes. Precursors of FDC may be present in low numbers in blood and bone marrow (Haley et al., 1995, *Adv. Exp. Med. Biol.* 378: 289–91). For example, in the non-adherent mononuclear blood cell fraction, separated at a density of 1.077 g/ml in a density gradient, only 0.1 per million of the cells revealed staining with dendritic cell marker Ki-M4 (Parwaresch et al., 1983, *Blood* 62:585–90).

We have discovered that certain soluble tumor antigens, shed from tumor cells of solid, non-lymphoid tumors, are capable of inducing an immune response which promotes tumor progression (one or more of tumor growth, invasion, and metastasis). This mechanism of promotion of tumor progression involves the specific type of immune response induced by shed tumor antigen. This specific immune response, a "pro-tumor immune response", may involve (a) the contact or presence of shed tumor antigen in relation to the cell surface of B cells, such as by antigen itself or as presented by follicular dendritic cells or other antigen presenting cells; (b) activation of such B cells to proliferate, and to differentiate into plasma cells which secrete anti-shed tumor antigen antibody; and (c) formation of immune complexes, comprising anti-shed tumor antigen antibody complexed to shed tumor antigen, which may act indirectly (via immune effector cells) and/or directly (on the tumor cells) to mediate tumor progression. Also, we have developed various compositions and methods for treating a pro-tumor immune response.

Therefore, a need exists for methods which may be used to screen for the possible presence of a pro-tumor immune response in an individual; particularly in an individual who has a solid, non-lymphoid tumor, or an individual who is at high risk (e.g., environmentally and/or genetically) for developing a solid, non-lymphoid tumor, or an individual who has been treated for a solid, non-lymphoid tumor and thereby inherently carries a risk of recurrence.

SUMMARY OF THE INVENTION

According to a primary object of the present invention, determined is an amount of mononuclear cell phenotype by a method in which one or more determinants, expressed by cells of the one or more selected subpopulations comprising mononuclear cell phenotype, is specifically bound by one or more detector molecules, thereby facilitating detection of an altered mononuclear cell phenotype, if present.

It is another object of the present invention to provide a method for screening for a pro-tumor immune response in an individual by determining an amount of mononuclear cell phenotype present in lymphoid tissue regional or distal to an organ which is (or was) the site of primary tumor in the individual. An amount of cells comprising an altered mononuclear cell phenotype, may comprise a diagnostic value, and may be an indicator for the presence of a pro-tumor immune response.

It is an additional object of the present invention to provide a method for screening for a pro-tumor immune response in an individual by determining an amount of mononuclear cell phenotype circulating in one or more body fluids of the individual (e.g., peripheral blood, or an effusion). In that regard, an amount of cells comprising an altered mononuclear cell phenotype, may comprise a diagnostic value, and may be an indicator for the presence of a pro-tumor immune response.

It is another object of the present invention to provide a method for providing a prognosis for an individual having a pro-tumor immune response by determining an amount of mononuclear cell phenotype present in a clinical sample obtained from the individual, and comparing the amount of mononuclear cell phenotype with a reference value (predetermined normal control value, or earlier value from the same individual) wherein the presence of an altered mononuclear cell phenotype may comprise a prognostic value, and may be an indicator for the state of the pro-tumor immune response.

According to a further object of the present invention, assay kits are provided for performing the above described methods. The assay kits may include various components, depending on the complexity of the type of method utilized for determining an amount of mononuclear cell phenotype. Assay kits would typically contain one or more reagents, with each reagent comprising a detector molecule capable of binding to a determinant that is expressed by mononuclear cell phenotype, and which facilitates detecting mononuclear cell phenotype present in the sample analyzed. In a preferred embodiment, an assay kit may comprise components selected from the group consisting of one or more reagents for detecting B lymphocytes (e.g., by a pan B cell marker), one or more reagents for detecting T lymphocytes (e.g., by a pan T cell marker), one or more reagents for detecting a functional marker of a mononuclear cell subpopulation (by a "functional mononuclear cell marker")(e.g., characteristic of memory, or of activation, or of binding a shed tumor antigen, or for purposes of detecting a mononuclear cell subpopulation according to the present invention, and a combination thereof), one or more reagents for detecting FDC (e.g., by a pan FDC marker), and a combination thereof; and may further comprise one or more standards for use in the method for determining an amount of mononuclear cell phenotype (and including for an altered mononuclear cell phenotype), one or more controls for use in the method for determining an amount of mononuclear cell phenotype (and including for an altered mononuclear cell phenotype), instructions for use of the assay kit and components, and a combination thereof.

The foregoing objects are achieved because of: (a) the discovery of a novel mechanism, a pro-tumor immune response, that may be involved in the promotion of tumor progression; and (b) an unexpected demonstration that there may exist mononuclear cell phenotype (e.g., one or more subpopulations) that may be present and that may differ in amounts ("altered mononuclear cell phenotype") in individuals having a pro-tumor immune response, as compared to that present in healthy controls. Thus, determined from a clinical sample is an amount of a mononuclear cell phenotype, and the resultant amount may be used as in determining a diagnostic value or prognostic value that may be used as an indicator relative to a pro-tumor immune response. For example, altered mononuclear cell phenotype comprising alterations in an amount of one or more B cell subpopulations, when detected in a diagnostic value, can be used as a screening tool for identifying individuals that may have a pro-tumor immune response (e.g., tumor and a pro-tumor immune response, or a pro-tumor immune response in absence of detectable tumor). Altered mononuclear cell phenotype comprising alterations in an amount of one or more T cell subpopulations, when detected in a diagnostic value, can be used as a screening tool for identifying individuals that may have a pro-tumor immune response. Altered mononuclear cell phenotype comprising alterations in an amount of one or more follicular dendritic cell subpopulations, when detected in a diagnostic value, can be used as a screening tool for identifying individuals that may have a pro-tumor immune response. For purposes of diagnostic or prognostic use, altered mononuclear cell phenotype may also comprise a combination of alterations. For example, altered mononuclear cell phenotype may comprise a combination comprising: (a) alterations in the amounts of one or more B cell subpopulations and of one or more T cell subpopulations; (b) alterations in amounts of one or more B cell subpopulations, of one or more T cell subpopulations, and of one or more FDC subpopulations; (c) alterations in the amounts of one or more B cell subpopulations and of one or more FDC subpopulations; and (d) alterations in the amounts of one or more T cell subpopulations and of one or more alterations in FDC subpopulations.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
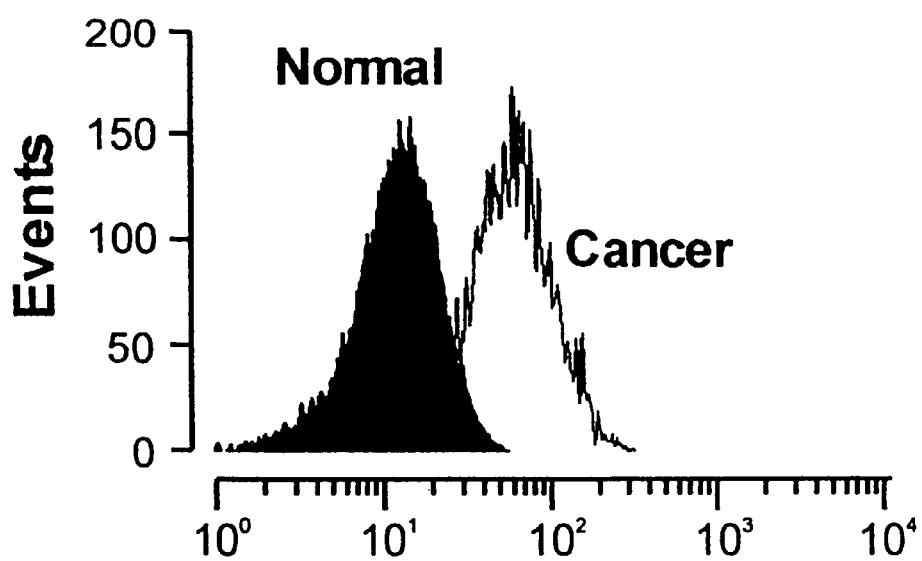
FIG. 1 is a histogram illustrating CD21+ expression (Normal) as compared to CD21+ hyperexpression, termed "CD21++", (Cancer) in B cells.

The term "mononuclear cell phenotype" is used herein, for purposes of the specification and claims, to mean a mononuclear cell subpopulation selected from the group consisting of sTn+ B cells, sTn+ B1 cells, memory B cells, sTn+ memory B cells, sTn+ T cells, sTn+ FDC, a combination thereof; and may also comprise a combination selected from the group consisting of an overall subpopulation of B cells (e.g., CD19+ cells) and one or more mononuclear cell subpopulations, an overall population of FDCs (e.g., CD19− CD21+ cells) and one or more mononuclear cell subpopulations, and a combination thereof.

The term "affinity ligand" is used herein, for purposes of the specification and claims, to mean a molecule which has binding specificity and avidity for a determinant associated with, and which can be used for diagnostic and/or prognostic detection of, mononuclear cell phenotype. For example, one type of affinity ligand, specific for a pan B cell marker (e.g., CD19+), may be used alone to detect an overall B cell subpopulation (e.g., CD19+ cells). This type of pan B cell marker may also be used in combination with other affinity ligands (e.g., specific for CD21+) to detect memory B cells (e.g., CD19+ CD21+ cells). In general, affinity ligands are known to those skilled in the art to include, but are not limited to, lectins, antibodies, immunoreactive fragments produced or derivatives derived from antibodies, peptides, and aptamers (see, e.g., U.S. Pat. No. 5,789,157). Immunoreactive fragments produced or derivatives derived from an antibody molecule are fragments which retain all or a portion of the binding function of the whole antibody molecule, and are known to those skilled in the art to include F(ab')$_2$, Fab', Fab, Fv, scFV, Fd' and Fd fragments. Methods for producing the various fragments from MAbs are well known in the art. For example, F(ab')$_2$ can be produced by pepsin digestion of the monoclonal antibody, and Fab' may be produced by reducing the disulfide bridges of F(ab')$_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. In a preferred embodiment, affinity ligands may include, but are not limited to, one or more of: anti-CD19 antibody, anti-CD20 antibody, anti-CD21 antibody, anti-CD22 antibody, anti-sTn antibody, anti-CD5 antibody, Lym-1 antibody (antibody against the B cell determinant recognized by Lym-1; see, e.g., U.S. Pat. No. 5,789,554), CDIM antibody (antibody against the B cell determinant recognized by CDIM; see, e.g., U.S. Pat. No. 5,593,676), anti-CD45R (RAhi or RO) antibody, anti-Ki-M4 antibody, and anti-DRC-1 antibody. A "detector molecule" is used herein to refer to an affinity ligand which has been coupled (using covalent or noncovalent or other means known in the art) to a detectable moiety. The term "detectable moiety" is used herein, for purposes of the specification and claims, to mean a label molecule that is directly or indirectly detectable and, as part of the detector molecule, may be used to determine an amount of mononuclear cell phenotype, if present, in a sample. Detectable moieties may include, but not limited to, enzymes (e.g., peroxidase, alkaline phosphatase, etc.), radioisotopes, haptens (e.g., biotin, avidin, etc.), chromophores, fluorescent molecules, and fluorescent nanocrystals, as known to those skilled in the art of diagnostics. In a preferred embodiment, the detectable moiety comprises a fluorescent molecule comprising: water-soluble functionalized quantum dots (e.g., CdSe core, ZnS shell); or a fluorophore which may include, but is not limited to, fluorescein (isothiocyanate), fluorescein derivatives, pthalocyanine dyes, phycoerythrin, up-converting phosphors, peridinin-chlorophyll protein, fluorescamine, dansyl chloride, rhodamine, Texas red tandem, phycocyanin tandem, allophycocyanin tandem, and coumarin derivatives. The detectable moiety may be bound to a primary affinity ligand; or to a secondary affinity ligand which is then used to specifically bind to an unlabelled primary affinity ligand (e.g., a combination of primary antibody, and labeled secondary antibody).

The term "clinical sample" is used herein, for purposes of the specification and claims, to mean a fluid or tissue obtained from an individual; and in a preferred embodiment, is selected from the group consisting of peripheral blood, body fluids other than peripheral blood (particularly effusions associated with solid, non-lymphoid tumors), and lymphoid tissue. The term "clinical sample" also encompasses a preparation which is derived from the clinical sample, and which is enriched for mononuclear cells or for one or more subpopulation of mononuclear cells comprising mononuclear cell phenotype, as will be more apparent from the following descriptions. For example, the term "peripheral blood" also encompasses a preparation which is derived from peripheral blood, wherein the preparation is enriched for mononuclear cells or for one or more mononuclear cell subpopulations comprising mononuclear cell phenotype, as will be more apparent from the following descriptions.

The term "determinant" with reference to the mononuclear cell phenotype to be detected, is used herein, for purposes of the specification and claims, to mean a cell-associated molecule which may be used to detect and determine an amount of cells comprising mononuclear cell phenotype in a clinical sample; wherein each determinant is capable of binding to an affinity ligand (or detector molecule) having binding specificity and avidity for that determinant. As an illustrative example of a preferred embodiment, and as will be apparent to one skilled in the art from the following descriptions, a combination of determinants may be used to detect one or more mononuclear cell subpopulations comprising mononuclear phenotype. Determinants may include, but are not limited to, molecules (e.g., receptors, components, antigen, or shed tumor antigen) present on the cell surface of one or more subpopulations comprising mononuclear cell phenotype, or molecules internal to such cells, or a combination thereof. In general, a determinant may be used alone or in combination with one or more other determinants to distinguish a particular mononuclear cell subpopulation comprising mononuclear cell phenotype from other subpopulations of cells which may be contained in the sample. In a preferred embodiment, the determinant may be selected from the group consisting of a pan B cell marker (e.g., CD19, CD20, CD72, and the like), a pan T cell marker (e.g., CD5 in absence of detectable CD19, and the like), a pan FDC marker (e.g., CD21 in absence of detectable CD19; Ki-M4; DRC-1; HJ2; R4/23; FDC-M1; BU-10; CAN.42; and the like), and a functional mononuclear cell marker (e.g., sTn, CD21++, CD5 in presence of CD19, CD21 in the presence of CD19, shed tumor antigen (e.g., detected as sTn) and the like), and a combination thereof. In a preferred embodiment, the determinant may be selected from the group consisting of CD19, CD21, CD5, sTn, and a combination thereof. As an illustrative example, a subpopulation comprising memory B cells (defined herein as CD5− B cells comprising mature B cells, or antigen-stimulated B lymphocytes, or progeny thereof which are not antibody secretors) comprising a mononuclear cell phenotype can be detected by detecting a combination of at least two determinants, wherein a first determinant comprises a pan B cell marker (e.g., CD19, CD20, CD72, and the like), and a second determinant comprises a functional mononuclear cell marker for memory B cells (e.g., CD21, CD79 (a or b), CD75 (e.g., CDw75), CD45R (CD45RAhi or CD45RO) and CD22). A third determinant, comprising an additional functional mononuclear cell marker comprising sTn, may be used. As an illustrative example, a subpopulation comprising B1 cells comprising a mononuclear cell phenotype can be detected by a combination of at least two determinants, wherein a first determinant comprises a pan B cell marker (e.g., CD19, CD20, CD72, and the like), and a second determinant comprises a functional mononuclear cell marker for B1 cells (e.g., CD5). A third determinant comprising an another functional mononuclear cell marker, sTn, may also be used. As an illustrative example, a subpopulation comprising T cells comprising a mononuclear cell phenotype can be detected by a combination of at least two determinants, wherein a first determinant comprises a pan T cell marker (e.g., CD3, or CD5 in absence of detectable CD19, or functional equivalent), and a functional mononuclear cell marker determinant comprising sTn. As an illustrative example, a subpopulation comprising follicular dendritic cells comprising a mononuclear cell phenotype can be detected by a combination of at least two determinants, wherein a first determinant comprises a pan FDC marker (e.g., CD21 in absence of detectable CD19; Ki-M4; DRC-1; HJ2; R4/23; FDC-M1; BU-10; or CAN.42), and a functional mononuclear cell marker determinant comprising sTn. While not intending to be bound by theory, the sTn detected on sTn+ T cells is believed to be primarily due to the presence of CD45 expressing an sTn epitope (as expressed in certain activated T cells), rather than shed tumor antigen being detected as associated with the cell surface; and sTn detected on mononuclear cells other than T cells is believed to be primarily due to the presence of an activation marker that is CD45 or like CD45 in that an sTn epitope is expressed and detected, but may also be due to the presence of a shed tumor antigen expressing sTn that may be associated with the cell surface.

The term "CD21++" is used herein, for purposes of the specification and claims, to mean a hyperexpression of CD21 as compared to the amount of CD21 normally present on B cells ("CD21+"). For purposes of illustration, CD21++ comprises a relative cell expression of CD21 which is equal to or greater than 3 times the normal relative B cell expression of CD21 (CD21+). For example, as measured by flow cytometry and in plotting the log intensity of CD21 staining of CD19+ cells, the average CD21 staining intensity of CD19+ cells of lymphoid tissue origin from individuals having tumor and a pro-tumor immune response was about 65; whereas the average CD21 staining intensity of CD19+ cells of lymphoid tissue origin from control individuals (not having a pro-tumor immune response) was about 15. In continuing this example, CD21++ was distinguished from CD21+ cells by setting as a lower limit of the range of CD21++ a value which is higher than 95% of the CD21+ values as expressed by CD21+ B cells of healthy donors (see FIG. 1).

The term "individual" is used herein, for purposes of the specification and claims, to mean a mammal, and preferably a human, and more preferably a human who is being screened for, or at risk of developing, or has developed, a pro-tumor immune response. This may include an individual having a primary tumor comprising a solid, non-lymphoid tumor and/or its metastases; an individual having a pre-cancerous lesion comprising transformed (abnormal in proliferation and/or genetic makeup as compared to normal epithelial cells of the same type) cells of epithelial origin which release shed tumor antigen; an individual who is at high risk (e.g., environmentally and/or genetically) for developing a solid, non-lymphoid tumor; or an individual who has been treated for a solid, non-lymphoid tumor and thereby inherently carries a risk of recurrence. A method according to the present invention is to screen for a pro-tumor immune response in such an individual at risk for developing, or who has developed, a pro-tumor immune response by detecting the presence or absence of an indicator comprising altered mononuclear cell phenotype. The presence of a pro-tumor immune response may also be an indicator for either tumor progression, or for susceptibility to tumor development.

The term "lymphoid tissue" is used herein, for purposes of the specification and claims, to mean a tissue which contains localized areas of antigen presenting cells (e.g., follicular or germinal center dendritic cells) and B lymphocytes, and in which can be induced an immune response involving B cells. An example of such localized areas comprises germinal centers. Such lymphoid tissues comprise lymphatic tissues including, but not limited to, lymph nodes; milky patches in the mesenterium of the intestine; omentum; appendix; Peyer's patches; loose connective tissue (e.g., associated with vessels in the walls of the aorta); lymphatic vessels; submucosal spaces; subserosa spaces; peritoneal cavity; ligaments (e.g., gastrohepatic ligament); artherosclerotic plaques containing trapped B cells; and epineura. "Lymphoid tissue" is inclusive of lymphoid tissues infiltrated with shed tumor antigen, which may become involved in a reactive process which includes an expansion in the size of germinal centers or germinal center equivalents, and an infiltration and/or proliferation of B cells, particularly memory B cells and shed tumor-antigen specific memory B cells. Generally, such lymphoid tissues may be found regional (draining) or distal to a primary tumor or its metastases. The term "lymphoid tissue" when used in reference as a sample from which the mononuclear cell phenotype is determined, also encompasses a preparation which is derived from the lymphoid tissue, and which is enriched for mononuclear cells or a subpopulation thereof, as will be more apparent from the following descriptions.

The term "amount" is used herein, for purposes of the specification and claims, a number which is expressive of a quantity of mononuclear cell phenotype (whether it be altered or normal) determined from a clinical sample. For example, the amount of mononuclear cell phenotype from the determination may be expressed as the actual (e.g., absolute) number of mononuclear cells of that phenotype by itself. Alternatively, amount from the determination may be expressed in relation to a certain parameter (as a relative value); e.g., number of mononuclear cells of that phenotype in relation to the quantity of blood or fluid (e.g., number of cells/ml), or number of mononuclear cells of that phenotype in relation to the number of a total cell population (e.g., percentage of the number of total white blood cells, or percentage of the number of overall B cells (where a B cell subpopulation is determined), or percentage of the number of overall T cells (where a T cell subpopulation is determined), or percentage of the number of total lymphocytes (where a B cell subpopulation or T cell subpopulation is determined), or percentage of number of mononuclear cells), or number of mononuclear cells of that phenotype in relation to a reference value (e.g., in relation to a predetermined clinical value).

The term "significant difference" is used herein relative to a reference value, for purposes of the specification and claims, to mean that the amount of the mononuclear cell phenotype determined in a sample falls outside the range of normal clinical values for that phenotype that is established by prospective and/or retrospective statistical clinical studies (the range of normal clinical values for that sample type comprising a "reference value"). Hence, such an amount of the mononuclear cell phenotype that is of a significant difference when compared to a reference value comprises an altered mononuclear cell phenotype, and may be an indicator of a pathological condition (e.g., solid, non-lymphoid tumor and a pro-tumor immune response, or a pro-tumor immune response). In a preferred use, the term "significant difference" is used herein, for purposes of the specification and claims, to mean that there is a statistically significant difference between an amount of the mononuclear cell phenotype determined ("first value") and an amount of the same mononuclear cell phenotype to which it is compared ("second value"). For example, a first value that is statistically significant different as compared to a second value may comprise the first value being a number that is at least about two standard deviations outside the mean of the second value. In one example, the first value and the second value may be obtained from the same individual at different points in time (e.g., to monitor the course (state) of the pathological condition, or to test the efficacy of treatment of the pathological condition) in obtaining an indicator comprising a "prognostic value". In another example, the first value and second value are obtained from different individuals. For example, a first value is determined from a clinical sample obtained from an individual being screened for a pro-tumor immune response, and a second value is a predetermined reference value (e.g., determined from analyses of an apparently healthy individuals or those lacking a pro-tumor immune response), in obtaining an indicator comprising a "diagnostic value". A statistically significant difference between an amount of a mononuclear cell phenotype in an individual having a pro-tumor immune response as compared to the amount comprising a reference value may be a difference represented by: $V_{rd} > Mean + 2.5(SEM)$, wherein "$V_{rd}$" is a value comprising an amount of the mononuclear cell phenotype determined from an individual having a pro-tumor immune response that is above the reference value for that phenotype (expressed as a Mean plus 2.5 times the standard error of the Mean); or by $V_{rd} < Mean - 2.5(SEM)$, where the amount of the mononuclear cell phenotype determined from an individual having a pro-tumor immune response is below the reference value, as will be more apparent from the following embodiments. In general, the methods of the present invention are used to generate indicators to identify individuals as having or lacking a pathological condition, in providing an additional parameter to a competent health professional in making a medical opinion.

The term "solid, non-lymphoid tumor" is used herein, for purposes of the specification and claims, to mean any primary tumor of ductal epithelial cell origin, including, but not limited to, tumors originating in the liver, lung, brain, bone marrow, breast, colon, pancreas, stomach, rectum, prostate, or reproductive tract (e.g., cervix, ovaries, endometrium etc.); and which produces shed tumor antigen (e.g., serous, or endometroid, or mucinous tumors). For purposes of the present invention, "solid, non-lymphoid tumor" may also include a melanoma which produces shed tumor antigen.

The term "shed tumor antigen" is used herein, for purposes of the specification and claims, to mean a glycomolecule (e.g., glycoprotein) which:

(a) by itself, or in an aggregated or oligomeric (two or more monomers which are together) form, has a molecular size equal to or greater than about 100 kilodaltons;

(b) is released (e.g., shed) from a primary non-lymphoid tumor or its metastases, thereby becoming soluble and allowing movement into lymphoid tissues regional or distal to the primary source;

(c) comprises an polyvalent molecule which has repeated or multiple subunits (e.g., repeated carbohydrate chains), each subunit containing one or more epitopes available for binding to anti-shed tumor antigen antibody, wherein the epitope comprises one or more of Tn antigen, sTn antigen, a terminal sialic acid-containing epitope other than sTn antigen, or a terminal GalNAC-containing epitope other than Tn;

(d) is produced by cells in a pattern of altered glycosylation (e.g., underglycosylated, incompletely glycosylated, or partially deglycosylated form) as compared to the glycosylation pattern of the same molecule typically found exposed on most normal cells (e.g., nonmalignant cells or non-precancerous cells, or cells not involved in an autoimmune disease process);

(e) is capable of inducing a humoral immune response resulting in the production and secretion of anti-shed tumor antigen antibody which is predominately of an IgG class (suggestive of, at least in part, a T independent antibody response); and (f) can interact with anti-shed antigen antibody in forming immune complexes, wherein the immune complexes may bind and crosslink Fc receptors (FcR) present on the surface of FcR-expressing cells.

With regard to the tumor antigen being soluble, the tumor antigen is non-cellular ("shed") tumor. Non-cellular tumor antigen comprises soluble tumor antigen that is not an integral part of a living tumor cell. Such shed tumor antigen exists in a form selected from the group consisting of free form (shed tumor antigen alone), in an immune complex form (shed tumor antigen bound to anti-shed tumor antigen antibody), in a form as presented on the surface of a follicular or germinal center dendritic cells (antigen presenting cell), in a form as bound to the cell surface of B cells, and as a form in tumor cell membranes existing apart from living tumor cells (i.e., soluble membrane complexes representing portions of dead tumor cells).

With regard to the shed tumor antigen being (a) a shed antigen (b) with repeated carbohydrate chains containing one or more epitopes, and (c) glycoprotein in composition, and for purposes of illustration, and not limitation, exemplifying such shed tumor antigen are mucins and mucin-like molecules. Briefly, mucins are high molecular weight glycoproteins (e.g., greater than about 100 kiloDaltons (kD) in molecular mass) of which a significant portion of the polypeptide backbone comprises a domain composed of a tandomly repeating peptide subunits (e.g. about 20 to about 125 repeats) which may be glycosylated. Mucins are found on normal ductal epithelial cells in sequestered locations that are not normally exposed to the immune system (e.g., restricted to the lumen of duct). However, in processes such as transformation (e.g., pre-cancerous) or tumor development, and due to various factors (e.g., the increased production of mucin, lack of availability of glycosyltransferases), tumor cells produce mucin in a form of altered glycosylation (e.g., underglycosylated or incompletely glycosylated; and e.g., with an exposed Tn antigen, or with a terminal or exposed sialic acid epitope). Thus, because of the altered glycosylation in growing tumors, the shed tumor mucin has one or more epitopes not normally found on mucin or has one or more epitopes which may be found on mucin but which is not normally exposed to the immune system. Such epitopes may include carbohydrate epitopes comprising the sialyl Tn (sTn) antigen (substantially comprising the NeuAc portion of NeuAcα2→6GalNAcα1→O-X- (X=Ser or Thr); or the Tn antigen (comprising the GalNAc portion of GalNAcα1→O-X-); or the shed tumor antigen may comprise other sialic acid containing epitopes (e.g., substantially comprising terminal NeuAcα2 on the carbohydrate chains (a) NeuAcα2→6Gal→O-X-, (b) NeuAcα2→6Galβ1→4GlcNAc→ (e.g., as found on CEA shed by adenocarcinomas),(c) NeuAcα2→3Gal-O-X-, or (d) NeuAcα2→3GalNAc→O-X-); or a combination thereof (e.g., comprising both the sTn antigen and Tn antigen). In a preferred embodiment, the shed tumor antigen has terminal sTn epitopes, or other terminal sialic acid-containing epitopes, which are primarily involved in the pro-tumor immune response. An example of a mucin-like glycoprotein which is differentially glycosylated by tumor cells, and is shed by tumor cells, is SSEA-1 antigen.

Tumor-associated glycoproteins, and their characterization such as nature of carbohydrate chain structure and/or monoclonal antibody binding, are known to those skilled in the art. Tumor-associated glycoproteins which are known to those skilled in the art as being found in a soluble form include, but are not limited, to the human equivalents of those presented in Table 1.

TABLE 1

| Soluble-tumor Ag | Antibody | Characteristic |
|---|---|---|
| sialyl SSEA-1 ("SLX") | FH-6 | pancreatic, lung, gastric, ovarian, cervical adenocarcinomas |
| PA8-15 | mAb PA8-15 | pancreatic, gastrointestinal carcinoma |
| MUSE 11 | mAb MUSE 11 | adenocarcinoma, pancreatic cancer |
| Her-2/neu | mAb GFD-OA-p185-1 | various carcinomas |
| TA90 or U-TAA | mAb ADI-40F4 | melanoma |
| shed CEA | mAb BSRF-S-97 | various adenocarcinomas |
| KL-6 antigen | mAb K1-6 | various adenocarcinomas |

For purposes of illustration, and not limitation, in a preferred embodiment of the present invention, the shed tumor antigen comprises the gene product of the MUC-1 gene (also known as polymorphic epithelial mucin). Shed tumor antigen and anti-shed tumor antigen antibodies may form immune complexes that may have a threshold level for spacing and number of antibody molecules necessary for Fc receptor (e.g., FcγRI) crosslinking.

The term "pro-tumor immune response", for purposes of the specification and claims, means a humoral immune response against a terminal, repeated, antigenic, carbohydrate determinant of shed tumor antigen that results in immune complexes formed between antibody (particularly IgG) to shed tumor antigen, and shed tumor antigen. In a preferred embodiment, such determinant is sTn or other sialic acid-containing epitope. Such immune complexes may then promote tumor progression by one or more mechanisms including, but not limited to: binding and crosslinking Fc receptors (e.g., FcγRI) on immune effector cells resulting in the release of inflammatory mediators which promote angiogenesis for, and invasion by, tumor cells; binding and crosslinking FcγRI on FcγRI-expressing tumor cells resulting in an induction of tumor cell proliferation, and an increase in the amount of shed tumor antigen released by the tumor cells; and binding and crosslinking Fc receptors (e.g., FcγRI) on Fc receptor expressing endothelial cells resulting in an induction of endothelial cell proliferation and/or release of factors promoting angiogenesis. Immune effector cells are host cells which are mediators of inflammation and/or angiogenesis (e.g., one or more of granulocytes, macrophages, vascular endothelial cells) that are capable of inducing a cascade of processes which promote tumor progression. For example, granulocytes and/or macrophages which are activated (crosslinked) by the immune complexes may be induced to release tissue degradative enzymes which breakdown the connective tissue matrix, thereby facilitating invasion of the tumor and spread of metastases beyond the primary tumor.

Measurement and quantitation of cell subpopulations in a clinical sample obtained from an individual can be important in assessing certain pathological conditions. Direct measurement of such subpopulations may provide an accurate assessment of the condition of, or susceptibility to, disease in the individual at the time the sample is taken. For example, the number of CD4+ T helper cells in peripheral blood has been used as an indicator of progression of HIV infection, and for monitoring treatment of the disease, in an individual. However, currently the prognosis of a tumor bearing individual who undergoes anticancer therapy (one or more of surgery, chemotherapy, immunotherapy, photodynamic therapy, radiotherapy, and the like) is mainly determined by the extent of residual tumor load, comprising either primary tumor and/or presence of micro-metastases (occult to current imaging techniques), following anticancer therapy. While detection of primary tumor cells and metastatic tumor cells may provide information clinically significant to the tumor bearing individual, the presence of such cells may not be an accurate predictor of further tumor development (recurrence), nor an accurate predictor if the individual can mount, or has mounted, an effective antitumor immune response. Further, presently there are no commercially available tests to evaluate for the presence of a pro-tumor immune response. There is a need for laboratory tests that distinguish an individual whom is more likely to have a favorable prognosis (e.g., one or more of stable remission; limited, localized disease progression; response to anticancer therapy that reduces the rate of recurrence of cancer) from an individual whom is likely to have an unfavorable prognosis (e.g., an individual having undergone anti-cancer therapy but whom still has indications of a pro-tumor immune response, and is at risk for recurrence; an individual having both tumor and a pro-tumor immune response; or an individual whom has a pro-tumor immune response that is advancing/progressing).

In that regard, the present invention relates to a discovery that one or more alterations in mononuclear cell phenotype ("altered mononuclear cell phenotype") can be present in individuals having tumor and a pro-tumor immune response, and in individuals having a pro-tumor immune response (e.g., after removal or reduction of substantially all tumor mass; or during a pre-cancerous condition such as before detectable tumor). An alteration may comprise a significant difference in an amount of one or more mono-nuclear cell subpopulations comprising mononuclear cell phenotype, as compared to a reference value for that phenotype. In a preferred embodiment of the present invention, an indicator for the presence of a pro-tumor immune response may comprise detection of altered mononuclear cell phenotype in one or more of (a) peripheral blood, (b) body fluids other than peripheral blood (particularly cell-containing effusions associated with solid, non-lymphoid tumors), and (c) lymphoid tissues containing deposits of shed tumor antigen. Thus, in the diagnostic methods and prognostic methods of the present invention, a clinical sample is assayed to determine an amount of mononuclear cell phenotype, and whether the amount of mononuclear cell phenotype determined is altered (e.g., increased or decreased) with respect to a reference value for that phenotype.

In one embodiment of the present invention, an altered mononuclear cell phenotype that comprises an indicator (comprising a diagnostic value) for the presence of a pro-tumor immune response (tumor and a pro-tumor immune response, or a pro-tumor immune response in absence of detectable tumor) in an individual may comprise a determination of a significant decrease in an amount of the overall subpopulation of B cells in the peripheral blood (e.g., B cells measured by using a pan B cell marker) as compared to a reference value (comprising a normal range of clinical values), combined with an alteration in a mono-nuclear cell subpopulation other than overall B cells. As one illustrative, non-limiting but preferred example, an altered mononuclear cell phenotype comprising the indicator may comprise a decrease in amount of peripheral blood B cells, in combination with an increase in an amount of one or more B cell subpopulations (e.g., sTn+ B cells, memory or mature B cells (e.g. CD19+ CD21+ cells), CD21++ memory or mature B cells, sTn+ B1 cells (e.g., CD19+ CD5+ sTn+ cells)) determined from peripheral blood and which amount is significantly different compared to the reference value for the respective one or more B cell subpopulations. Alternatively, the indicator may comprise an alteration in one or more mononuclear cell subpopulations, other than an overall B cell type subpopulation or an overall FDC subpopulation in lymphoid tissue, comprising mononuclear cell phenotype. As a preferred illustration, an altered mononuclear cell phenotype comprising the indicator may comprise an increase in an amount (with respect to a respective reference value) of a mononuclear cell subpopulation selected from the group consisting of sTn+ T cells, overall FDC in peripheral blood, sTn+ FDC, sTn+ B cells (e.g., CD19+ sTn+ cells), memory B cells (e.g., CD19+ CD21+ cells), CD21++ memory B cells (e.g., CD19+ CD21++ cells), sTn+ B1 cells (e.g., CD19+ CD5+ sTn+ cells), and a combination thereof. Such an indicator may further comprise a decrease in an amount (with respect to a respective reference value) of a peripheral blood mononuclear cell subpopulation selected from the group consisting of sTn+ memory B cells (e.g., CD19+ CD21+ sTn+ cells). A preferred altered mononuclear cell phenotype may be determined and used as an indicator to the exclusion of altered mononuclear cell phenotype other than the preferred phenotype.

In another example, an indicator comprising a prognostic value for an individual who has had substantially all or a majority of tumor mass removed or reduced by anticancer therapy comprises determining an amount, in successive samples (e.g., one or more samples pre-anticancer therapy, and one or more samples post-anticancer therapy) from the individual of one or more mononuclear cell sub-populations comprising mononuclear cell phenotype. By comparing the effect of anticancer therapy on the amount of the respective mononuclear cell phenotype, prognostic information or information relating to the efficacy of the therapy (including possible need for modification of the treatment regimen) may be obtained. As an illustrative example, an individual undergoing anticancer therapy, as determined from one or more samples post-anticancer therapy, may show one of several patterns of altered mononuclear cell phenotypes. In one preferred embodiment where a pro-tumor immune response still exists after anticancer therapy, detected in a body fluid, preferably peripheral blood, sample obtained from the individual post-treatment may be a continuing presence of altered mononuclear cell phenotype. The altered mononuclear cell phenotype may be compared to a reference value for that mononuclear cell phenotype (including sample type), wherein the reference value is selected from the group consisting of a normal range of clinical values, a value obtained from the same individual pretreatment, a value obtained from the same individual during treatment but before conclusion of treatment, and a combination thereof. For example, and as an illustrative, non-limiting and preferred example, the altered mononuclear cell phenotype may comprise a subpopulation selected from the group consisting of (expressed as an amount relative to the respective reference value comprising a normal range of clinical values for the subpopulation determined): an increase in sTn+ B cells, an increase in CD21+ B cells, an increase in CD21++ B cells, a decrease in CD21+ sTn+ B cells, an increase in sTn+ B1 cells, an increase in sTn+ T cells, an increase in sTn+ follicular dendritic cells, an increase in peripheral blood FDC, a decrease in sTn+ CD21+ B cells (e.g., CD19+ CD21+ sTn+ cells), and a combination thereof. Such altered mononuclear cell phenotype may be an indicator of prognostic value that anticancer therapy was ineffective in substantially reducing the pro-tumor immune response. Thus, the individual may have an increased risk of recurrence due to the continued presence of the pro-tumor immune response (hence, a prognostic value); and may be a candidate for further therapy that is targeted to substantially reducing the pro-tumor immune response. A preferred altered mononuclear cell phenotype may be determined and used as a prognostic indicator to the exclusion of altered mononuclear cell phenotype other than the preferred phenotype.

In an illustrative example wherein substantial reduction of a pro-tumor immune response (either with substantial reduction of tumor, or by itself) has been achieved, detected in a clinical sample obtained post-anticancer therapy from the individual is a significant difference in an amount of mononuclear cell phenotype ("second value") as compared to an amount determined for that respective phenotype from the same type of clinical sample wherein the sample was obtained from the same individual before anticancer therapy was begun or before it is concluded ("first value"). In continuing this embodiment, the second value, in significantly differing from and when compared to the first value, approaches or falls within the reference value (comprising a normal range of clinical values) for that mononuclear cell phenotype (see, e.g., Example 4, and FIG. 3, herein). Detection of such a change in mononuclear cell phenotype as a result of anticancer therapy may be indicative of the individual's positive response to anticancer therapy, and may also be an indicator that this individual has a reduced chance of recurrence as compared to an individual who demonstrates no significant difference in (e.g., where the second value does not differ from the first value), or demonstrates a worsening of (e.g., where the second value deviates farther outside the reference value than the first value), the pro-tumor immune response subsequent to anticancer therapy.

In accordance with one embodiment of the method for screening for a pro-tumor immune response according to the present invention, the method comprises: (a) contacting a clinical sample, obtained from the individual, with one or more detector molecules for detecting, and then determining the amount of (e.g., by detecting and quantifying an amount of cells in the sample which are bound by the one or more detector molecules), mononuclear cell phenotype in the sample; and (b) comparing the amount of mononuclear cell phenotype determined in the sample to a reference value for the mononuclear cell phenotype; wherein a significant difference in the amount of mononuclear cell phenotype determined as compared to the reference value may be an indicator of the presence of a pro-tumor immune response. Preferably, substantially the same methodology used to determine the mononuclear cell phenotype from the sample being screened is used to determine the mononuclear cell phenotype comprising the reference interval. The significant difference in amount of mononuclear cell phenotype determined comprises an altered mononuclear cell phenotype. In a preferred embodiment, when the clinical sample comprises a body fluid such as peripheral blood, the altered mononuclear cell phenotype may comprise a subpopulation selected from the group consisting of (expressed as an amount relative to the respective reference value for the subpopulation determined): an increase in sTn+ B cells, an increase in CD21+ B cells, an increase in CD21++ B cells, a decrease in CD21+ sTn+ B cells, an increase in sTn+ B1 cells, an increase in sTn+ T cells, an increase in sTn+ follicular dendritic cells, a increase in overall follicular dendritic cells, and a combination thereof. The altered mononuclear cell phenotype may further comprise a decrease in overall B cells (e.g., CD19+ cells). In another preferred embodiment in which the clinical sample comprises lymphoid tissue, the altered mononuclear cell phenotype may comprise a mononuclear cell subpopulation selected from the group consisting of (expressed as an amount relative to the respective reference value for the subpopulation determined): an increase in sTn+ B cells, an increase in CD21+ B cells, an increase in CD21++ B cells, an increase in sTn+ follicular dendritic cells, and a combination thereof. The altered mononuclear cell phenotype may further comprise an increase in overall B cells (e.g., CD19+ cells), an increase in overall FDC, and a combination thereof. A preferred altered mononuclear cell phenotype may be determined and used as an indicator to the exclusion of altered mononuclear cell phenotype other than the preferred phenotype.

In accordance with another embodiment of the method according to the present invention, the method comprises determining the state (e.g., progression or advancement, or reduction, or no change, in the course of) a pro-tumor immune response, at a certain point in time, in an individual having a pro-tumor immune response (either in the presence or absence of detectable tumor) by determining the amount of mononuclear cell phenotype in each of successive samples obtained from the individual. Hence, the state of the pro-tumor immune response in the individual is determined by comparing an amount of the mononuclear cell phenotype in a sample obtained from the individual for establishing a reference value for that particular individual's pro-tumor immune response (e.g., "reference sample") to an amount of the same type of mononuclear cell phenotype in a sample obtained from the individual subsequent to the reference sample ("test sample") in determining the state of the pro-tumor immune response at the time at which the test sample was obtained from the individual. The reference sample and test sample may be analyzed for their respective amount of mononuclear cell phenotype using essentially the same methodology. Preferably the reference sample and test sample comprise the same sample type; e.g., each sample comprises a sample of peripheral blood or each sample comprises a sample of lymphoid tissue. In illustrating this embodiment, the method comprises: (a) contacting a clinical sample comprising a test sample, obtained from the individual, with one or more detector molecules for detecting, and then determining the amount of (e.g., by detecting and quantifying an amount of cells in the test sample which are bound by the one or more detector molecules), mononuclear cell phenotype in the test sample; and (b) comparing the amount of mononuclear cell phenotype determined in the test sample to an amount of mononuclear cell phenotype determined in a reference sample obtained from the individual; wherein presence or absence of a difference between the amount of mononuclear cell phenotype in the test sample and the amount of mononuclear cell phenotype in the reference sample provides an indicator for the state of the pro-tumor immune response at a time at which the test sample was obtained from the individual. For example, when an amount of mononuclear cell phenotype determined from test sample is approximately the same (e.g., no significant difference) as the amount of mononuclear cell phenotype determined from the reference sample, such a result may be an indicator that the state of the individual's pro-tumor immune response is unchanged during the time period between the time at which the reference sample was obtained and the time at which the test sample was obtained. However, where the amount of mononuclear cell phenotype determined from test sample deviates farther away from a normal range of clinical values than does the amount of mononuclear cell phenotype determined from the reference sample, such a result is an indicator that the pro-tumor immune response has advanced (e.g., the pro-tumor immune response has progressed to a more pathological condition) during the time period between the time at which the reference sample was obtained and the time at which the test sample was obtained. Alternately, where the amount of mononuclear cell phenotype determined from test sample differs from the amount of mononuclear cell phenotype determined from the reference sample because the amount determined from the test sample approaches or falls within a normal range of clinical values for that mononuclear cell phenotype, such a result is an indicator that the pro-tumor immune response has been reduced (e.g., the pro-tumor immune response has decreased in intensity or has been suppressed) during the time period between the time at which the reference sample was obtained and the time at which the test sample was obtained. As previously discussed in more detail herein in which the prognostic method is used to monitor efficacy of anticancer therapy, the reference sample is generally obtained from the individual before anticancer therapy is initiated or in the initial period of treatment (before the therapy is expected to show any clinical effects), and the test sample is generally obtained at a point in time after anticancer therapy has been administered to the individual (e.g., including at or after the conclusion of a regimen of anticancer therapy). A preferred mononuclear cell phenotype (normal or altered) may be determined and used to determine the state of a pro-tumor immune response to the exclusion of mononuclear cell phenotype other than the preferred phenotype.

In a preferred embodiment of the methods according to the present invention, the one or more detector molecules for, and determining an amount of, mononuclear cell phenotype in a sample comprises a plurality of detector molecules selected from the group consisting of a detector molecule for detecting a pan B cell marker and a detector molecule for detecting a functional mononuclear cell marker comprising a determinant found on one or more B cell subpopulations (e.g., CD21, hyperexpressed CD21, CD5, sTn), one or more detector molecules for detecting a pan T cell marker and a detector molecule for detecting a functional mononuclear cell marker comprising sTn, one or more detector molecules for detecting a pan follicular dendritic cell marker and a detector molecule for detecting a functional mononuclear cell marker comprising sTn, and a combination thereof. In another preferred embodiment, the plurality of detector molecules used to determine a mononuclear cell phenotype comprising amounts of B cells, T cells, and follicular dendritic cells is a combination of detector molecules comprising a detector molecule for detecting a determinant comprising CD19, a detector molecule for detecting a determinant comprising CD21, a detector molecule for detecting a determinant comprising CD5, and a detector molecule for detecting a determinant comprising sTn.

Additionally, test kits are provided for determining an amount of mononuclear cell phenotype in a clinical sample. Since we have devised several methods for treating a pro-tumor immune response in an individual, by detecting a pro-tumor immune response in an individual, various treatment options may be made available to the individual.

For purpose s of the description, the methods and compositions of the present invention will be illustrated in the following examples.

EXAMPLE 1

This Example illustrates that a clinical sample to be tested for an amount of mononuclear cell phenotype may be used as obtained, or may processed in a manner that includes, but is not limited to, enrichment for mononuclear cells ( e.g., containing lymphocyte populations such as T cells and B cells and follicular dendritic cells), and enrichment for lymphocyte subpopulation (e.g., B cells, or T cells or B cells and T cells). Methods of enriching a clinical sample, such as a sample of peripheral blood, for mononuclear cells are well known in the art. For example, mononuclear cells may be isolated from a clinical sample by overlaying the sample on a density gradient medium (e.g., Ficoll-Hypaque or Percoll or Lymphocyte Separation Medium) and then performing density gradient centrifugation. Depending on the density gradient medium used, typically the mononuclear cells may be harvested from the interface or buffy layer of the gradient.

The mononuclear cell population may be further processed to obtain a cell subpopulation enriched in B cells using one of several methods known to those skilled in the art. For example, neuraminidase-treated sheep red blood cells may be added to the mononuclear cell population, and the mixture may be centrifuged in a density gradient medium. T cells will bind (rosette) with the sheep red blood cells, and therefore are found in the cell pellet. In contrast, a lymphocyte subpopulation enriched in B cells would remain at the interface and can be harvested. Alternatively, a lymphocyte subpopulation enriched in B cells may be obtained in a negative selection process. For example, the mononuclear cell population may be mixed with magnetic beads coated with one or more antibodies that bind to T lymphocytes (e.g., anti-CD2 mAb, anti-CD3 mAb, anti-CD4 mAb, anti-CD8 mAb, anti-CD28 mAb, or a combination thereof). A magnetic field is then applied, thereby immobilizing the T lymphocytes. The rest of the cell suspension (portion of the mononuclear cells which are not immmobilized) comprise a lymphocyte subpopulation enriched in B cells. The T cells may be eluted from the magnetic beads using methods known in the art; hence resulting in a positive selection and a preparation comprising a lymphocyte subpopulation enriched in T cells.

In a method of positive selection, a lymphocyte subpopulation enriched in B cells may be obtained from the clinical sample. For example, the clinical sample is mixed with magnetic beads coated with antibodies that bind to most B lymphocytes (e.g., anti-CD19 mAb, anti-CD20 mAb). A magnetic field is then applied, thereby immobilizing the B lymphocytes. The rest of the cell suspension (portion of the mononuclear cells which are not immobilized) may be used as a preparation enriched in mononuclear cells selected from the group consisting of T cells, FDC, or a combination thereof. The magnetic beads-B cell complex may be applied directly in an assay for quantitating B cells, or the B cells may first be eluted from the magnetic beads using methods known to those skilled in the art (e.g., competition with free ligand).

Generally, most FDC float at densities greater than 1.06 g/ml on low density albumin gradient or Percoll gradient or Ficoll-Urografin gradient (Schnizlein et al., 1985, *J. Immunol.* 134:1360–8; Petrasch et al., 1990, *Eur. J. Immunol.* 20:1013–8). A mononuclear cell population may be further processed to obtain a cell subpopulation enriched in FDC using one of several methods known to those skilled in the art. For example, opsonized sheep red blood cells may be added to the mononuclear cell population, and the mixture may be centrifuged in a density gradient medium. FDC will form rosettes with opsonized sheep red blood cells, and therefore are found in the cell pellet. Alternatively, a subpopulation enriched for FDC may be obtained in a double selection process. For example, the mononuclear cell population may be mixed with magnetic beads coated with one or more antibodies that bind to CD19+ cells. A magnetic field is then applied, thereby immobilizing populations of cells comprising B lymphocytes. The rest of the cell suspension (portion of the mononuclear cells which are not immmobilized) is removed, and then mixed with magnetic beads coated with one or more antibodies that bind to CD21+ cells. A magnetic field is then applied, thereby immobilizing populations of cells substantially comprising FDC (CD21+). The magnetic beads-FDC complex may be applied directly in an assay for quantitating FDC, or the FDC may first be eluted from the magnetic beads using methods known to those skilled in the art (e.g., competition with free ligand). Also, discontinuous gradient centrifugation and magnetic separation may be used in combination to isolate FDC. For example, mononuclear cells can be layered onto a discontinuous bovine albumin gradient, followed by centrifugation at 8500×g. The cells suspended at the 1.052 to 1.030 interphase are collected. Such cells are incubated with biotin labelled KiM4 mAb, then attached to streptavidin-conjugated paramagnetic beads, and then sorted using a magnetic sorter, thereby resulting in an average FDC content of 78% (Schmitz et al., 1993, *J.. Immunol. Methods* 26:189–196). Alternatively, flow cytometric cell sorting may be performed to isolate HJ2+ FDC.

EXAMPLE 2

This Example illustrates testing of a clinical sample by determining an amount of mononuclear cell phenotype contained therein. As apparent to those skilled in the art from the descriptions herein, testing can be performed by a process that includes, but is not limited to, immunofluorescence, chemiluminescence, flow cytometry, and a cell-based assay such as a cell-based enzyme-linked immunosorbent assay ("cELISA"). In a cELISA, the cells prepared from the clinical sample which are to be assay for the mononuclear cell phenotype to be determined are fixed to the wells of an ELISA plate. For example, each well of a 96 well plate may be incubated with a 100 μl of a solution of poly-L-lysine hydrobromide (5 mg/ml) in a buffered saline solution for 30 minutes at room temperature. After removing the solution, the cells (about 100,000 to 200,000/well) are plated, the plate is then centrifuged (e.g., at 100 g for 5 minutes), and the supernatant is then removed. Glutaraldehyde in buffer (0.25%) is added to each well, and then incubated for 5 minutes at room temperature. The wells containing fixed cells may then be washed with a Tris-buffered saline or other suitable solution, and detector molecules may then be added in accordance with an ELISA protocol in assaying for the mononuclear cell phenotype to be determined (e.g., incubation with one or more detector molecules, one or more washes, and subsequent detection of detector molecules bound to the fixed cells). As will be apparent to one skilled in the art, an amount of the mononuclear cell phenotype to be determined may be determined and expressed in relation to another parameter, as previously described herein in more detail. However, it will be apparent to one skilled in the art that the amount determined of a mononuclear cell phenotype may vary depending on factors which include, but are not limited to, the specific processes (methodology) used to determine the amount of mononuclear cell phenotype, the nature of the detector molecules used in the determination, the origin and processing of the clinical sample tested for the mononuclear cell phenotype, and the laboratory personnel and instruments used to perform the determination assays.

In a preferred and illustrative embodiment, flow cytometry is used to determine an amount of the mononuclear cell phenotype desired to be determined. The general principles involved in flow cytometry are well known in the art. Briefly, parameters that may be used in the assay include light scatter (e.g., to gate on one or more mononuclear cell subpopulations based on size, granularity and cell volume), fluorescence emission spectra and intensity thereof (to determine which detector molecules are bound and, hence which cells are present; and the amount of expression by a cell of the determinant bound by a detector molecule, and a number of cells in a sample which express that determinant). It is known to those skilled in the art that flow cytometry can detect cells specifically labeled with more than one type of fluorescent molecule.

In one embodiment of determining an amount of mononuclear cell phenotype in a clinical sample, mononuclear cells were isolated from the clinical sample using a density gradient medium and by density gradient centrifugation. Aliquots, each of approximately 1 million cells, were treated in one of several different ways. A first aliquot of cells was left unstained, so as to act as a control for possible autofluorescence. A second aliquot of cells was mixed in a staining process with isotype detector molecules. In that regard, it is widely accepted by those skilled in the art that a desirable control for setting the negative region markers (to account for the fluorescence due to non-specific background observed with the staining process) is to stain with a mAb of the same subclass as the mAb used in the testing, but with an irrelevant specificity (e.g., does not specifically recognize a determinant on the cells of the mononuclear cell phenotype to be determined), and is commonly referred to as an "isotype control". Thus, the second aliquot was mixed with an IgG1 control antibody labeled with FITC, an IgG1 control antibody labeled with Pe, and an IgG1 control antibody labeled with Pe-Cy5. This treated second aliquot serves as a negative control relative to any non-specific binding of the isotype (IgG1) antibodies to the cells to be detected. A third aliquot of cells may be stained with one or more detector molecules having binding specificity for the mononuclear cell phenotype to be determined. For example, and in continuing with this exemplary embodiment, the third aliquot of cells is double-stained (stained jointly) with anti-CD19 antibody (IgG1 mAb) labeled with Pe-Cy5, and an anti-CD21 antibody (IgG1 mAb) labeled with FITC. Additional aliquots may be stained with other combinations of detector molecules having binding specificity for cells of the mononuclear cell phenotype to be detected. For purposes of illustration, but not limitation, one such other combination is triple-staining of an aliquot comprising a staining with an anti-sTn antibody to detect B cells and/or follicular dendritic cells having a determinant comprising sTn on their cell surface (e.g., IgG1 murine mAb) including an incubation with a secondary rabbit anti-mouse IgG antibody labeled with Pe; and then a double-staining with anti-CD19 antibody (IgG1 mAb) labeled with Pe-Cy5, and an anti- CD21 antibody (IgG1 mAb) labeled with FITC (e.g., depending on the cell types present in the preparation being analyzed, to detect B cells comprising CD19+ CD21+ sTn+ cells, FDC comprising CD19– CD21+ sTn+ cells, or to detect both CD19+ CD21+ sTn+ cells and CD19– CD21+ sTn+ cells). Another exemplary combination is triple-staining of an aliquot comprising a staining with an anti-sTn antibody (e.g., IgG1 murine mAb) to detect sTn+ T cells, including an incubation with a secondary rabbit anti-mouse IgG antibody labeled with Pe, and then a double-staining with anti-CD19 antibody (IgG1 mAb) labeled with Pe-Cy5, and an anti-CD5 antibody (IgG1 mAb) labeled with FITC (e.g., to detect CD19– CD5+ sTn+ cells).

Any one of several available staining protocols may be used for cell staining. For example, for the first aliquot of cells which remain unstained, the cells were mixed with staining buffer alone (e.g., 50 μl of a physiologically acceptable buffer). The staining buffer utilized was phosphate buffered saline containing 2% fetal calf serum and 0.1% sodium azide. In general, and for contact and mixing an aliquot of cells with a detector molecule, the cells (e.g., sample volume ranging from 20 μl to 100 μl) are incubated with the one or more different, pre-titered detector molecules for 20–40 minutes at 4° C. After this incubation, the cells in the reaction mixture may be washed in physiologically acceptable buffer, and then may be diluted to a final volume for analysis on the flow cyto-meter. In continuing with this illustrative embodiment, the second aliquot of cells (as the negative control for the staining process) was mixed with staining buffer and with 1:10 dilutions of an isotype IgG1 labeled with FITC, an isotype IgG1 labeled with Pe, and an isotype IgG1 labeled with Pe-Cy5; and then incubated for 30 minutes in the dark at 4° C. The mixture was then centrifuged at 1500 rpm for 5 minutes. The supernatant was removed and a wash solution (e.g., 150 μl of a physiologically acceptable solution) was used to suspend the cell pellet, and then the mixture was centrifuged (a wash step). The wash step may be repeated one or more times. The cell pellet from the final wash is then taken up in a physiologically acceptable solution in a sufficient volume for flow cytometric analysis (e.g., 200–250 μl). The third aliquot of cells was double-stained using essentially the same protocol as for the second aliquot, except that the antibodies mixed with the cells of the third aliquot were the one or more detector molecules for detecting the mononuclear cell phenotype desired to be determined (e.g., anti-CD19 IgG1 mAb labeled with Pe-Cy5, and an anti-CD21 IgG1 mAb labeled with FITC; final dilution of each mAb was 1:10). In some cases, a fourth aliquot of cells were triple-stained as described above. For example, cells were first mixed and incubated with anti-sTn antibody (murine IgG1), and then washed; followed by mixing and incubating with a secondary rabbit anti-mouse IgG antibody labeled with Pe, and then washed; followed by a double-staining with anti-CD19 antibody labeled with Pe-Cy5, and an anti-CD21 antibody labeled with FITC, and then washed. A number of commercially available flow cytometers can be used as the instrument on which is performed the method of the present invention. Desirably, the flow cytometer has a single laser source; and in a preferred embodiment, the single laser source is an argon laser tuned at 488 nanometers (nm). Additionally, the flow cytometer is operatively connected to appropriate operating software and data management systems.

According to the method of the present invention, determined was an amount of mononuclear cell phenotype in clinical samples obtained from individuals having solid, non-lymphoid tumor and a pro-tumor immune response. Also determined was an amount of mononuclear cell phenotype in clinical samples obtained from apparently healthy individuals, from which determination may be established a reference value. In one illustration of this method, the clinical samples comprised peripheral blood obtained by venipuncture into blood collection tubes, wherein peripheral blood mononuclear cells were isolated and then analyzed; and the respective amounts were determined using flow cytometric methods by the techniques disclosed herein. For example, where mononuclear cell phenotype comprised one or more lymphocyte subpopulations, light scatter was used as a parameter to gate on primarily lymphocytes based on the size, granularity and cell volume of lymphocytes. In addition to gating for light scatter, each sample undergoing the staining process was gated for respective fluorescence emission(s). In continuing with this example, when an amount of memory B cells was determined by double-staining (e.g., for CD19 and CD21), the analysis was gated on those cells positive for CD19 expression as determined by detection of Pe-Cy5 fluorescent emission. In this analysis, CD19 positive lymphocytes were considered to represent the relative overall subpopulation of B cells in the clinical sample analyzed, and were expressed as a percentage of the number of white blood cells in the sample. CD19 positive lymphocytes were then gated for those cells also positive for CD21 expression as determined by detection of FITC fluorescent emission. Lymphocytes double stained for both CD19 and CD21 were considered to represent memory B cells. Such CD19+ CD21+ B cells were then expressed in an amount as a percentage of overall B cells by using the formula:

(the number of CD19+ CD21+ B cells/number of CD19+ B cells)×100.

A similar procedure was used to determine amounts of B cell subpopulations comprising CD19+ CD21++ cells; CD19+ sTn+ cells; and CD19+ CD21+ sTn+ cells (e.g., by triple staining).

In an illustration in which mononuclear cell phenotype comprised sTn+ T cells, after using light scatter to gate on primarily lymphocytes, an amount of overall T cells was determined using double-staining (e.g., CD19– and CD5+), wherein the analysis was gated on those cells positive for CD5 expression as determined by detection of FITC fluorescent emission. CD5 positive cells were then gated for those cells negative for CD19 expression as determined by the absence of detection of Pe-Cy5 fluorescent emission. Lymphocytes stained for CD5, but unstained for CD19, were considered to represent an overall subpopulation of T cells, and were expressed as a percentage of white blood cells in the sample. A similar procedure was used to determine an amount of CD19– CD5+ sTn+ T cells by triple staining with anti-sTn antibody with a secondary antibody labeled with Pe, anti-CD19 antibody labeled with Pe-Cy5, and anti-CD5 antibody labeled with FITC. Thus, an amount of CD19– CD5+ sTn+ cells was then expressed as a percentage of an overall T cell subpopulation (CD19– CD5+) by using the formula:

(the number of CD19– CD5+ sTn+ cells/number of CD19– CD5+ cells)×100.

In an illustration in which mononuclear cell phenotype comprised one or more follicular dendritic cell subpopulations, an amount of FDC was determined using double-staining (e.g., CD19– and CD21+), wherein the analysis was gated on those cells positive for CD21 expression as determined by detection of FITC fluorescent emission. CD21 positive nucleated cells were then gated for those cells negative for CD19 expression as determined by the absence of detection of Pe-Cy5 fluorescent emission. Nucleated cells stained for CD21, but unstained for CD19, were considered to represent FDC. An amount of CD19− CD21+ FDC was then expressed as a percentage of total nucleated cells ("nucleated events") by using the formula:

(the number of CD19− CD21+ FDC/number of nucleated events)× 100.

A similar procedure was used to determine an amount of CD19− CD21+ sTn+ FDC by triple staining with anti-sTn antibody with a secondary antibody labeled with Pe, anti-CD19 antibody labeled with Pe-Cy5, and anti-CD21 antibody labeled with FITC. Thus, an amount of CD19− CD21+ sTn+ FDC was then expressed as a percentage of total FDC (CD19− CD21+) by using the formula:

(the number of CD19− CD21+ sTn+ FDC/number of total FDC)× 100.

In an illustration of the method according to the present invention wherein lymphoid tissue was used as the clinical sample from which is determined an amount of mononuclear cell phenotype, lymphoid tissue samples were processed by cutting the tissue into thin sections, and performing an enzyme digestion (with collagenase, hyaluronidase, and DNase) to obtain a cell preparation. The cell preparation was then enriched for mononuclear cells using a process as described in Example 1 herein; and then stained and analyzed by flow cytometry using essentially the same methods as described herein for clinical samples comprising peripheral blood.

As previously disclosed herein, mononuclear cell phenotype may comprise one or more mononuclear cell subpopulations. Using the formulas and methods described herein, illustrated in Table 2 are amounts of respective mononuclear cells subpopulations ("MNC"), that may be determined using the method of the present invention. The mononuclear cell subpopulations were determined in clinical samples comprising peripheral blood ("PBL") or lymphoid tissue ("LT") from individuals having a pro-tumor immune response and solid, non-lymphoid tumor ("Tumor/PTIR"), and from healthy individuals lacking a pro-tumor immune response ("Reference value"). The amounts were expressed as the Mean percentage±standard error of the mean.

TABLE 2

Figure 2:
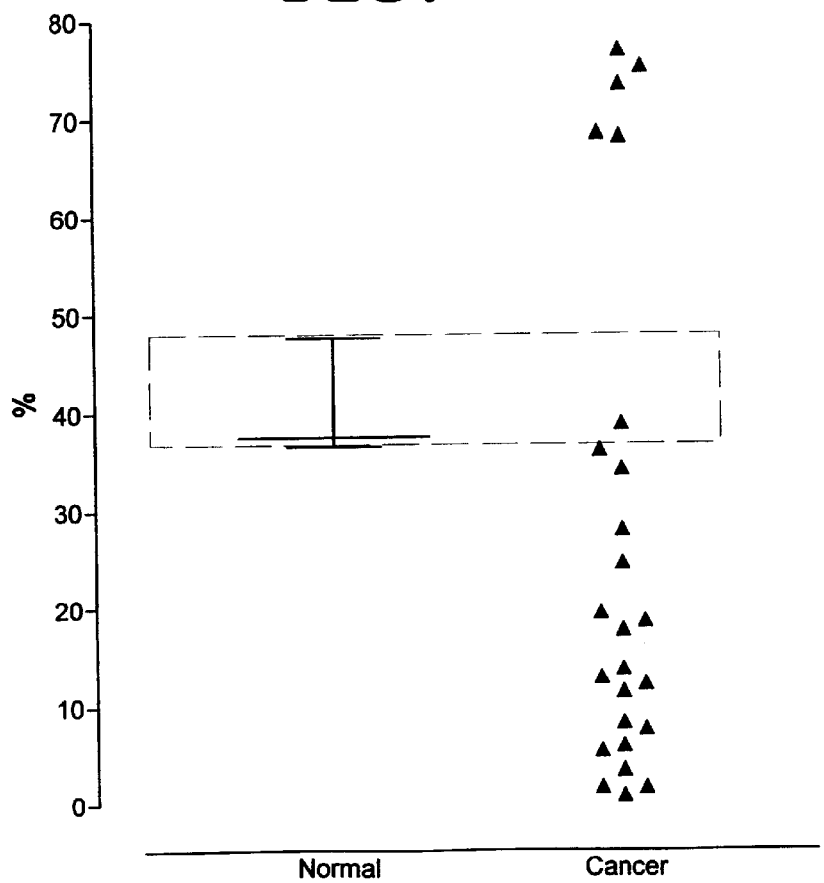
FIG. 2 is a bar graph illustrating an amount of sTn+ (CD19− CD21+ sTn+) FDC determined from lymphoid tissue of individuals having solid, non-lymphoid tumor and a pro-tumor immune response ("Cancer") as compared to a reference value (amount in healthy controls; "Normal").

| MNC | Reference value PBL | Tumor/ PTIR PBL | Reference value LT | Tumor/ PTIR LT |
|---|---|---|---|---|
| CD19 + | 12.7 ± 3.6 | 2.7 ± 0.5 | — | — |
| CD19 + sTn + | 1.3 ± 0.4 | 5.9 ± 1.5 | 9.1 ± 4.1 | 36.8 ± 4.8 |
| CD19 + CD21 + | 22.0 ± 3.6 | 58.2 ± 5.2 | 10.2 ± 4.4 | 69.8 ± 6.1 |
| CD19 + CD21 ++ | 3.8 ± 1.8 | 48.8 ± 5.3 | 1.1 ± 0.1 | 48.8 ± 5.3 |
| CD19 + CD 21 + sTn + | 29.7 ± 5.0 | 16.1 ± 3.7 | — | — |
| CD19 + CD5 + | 1.8 ± 0.9 | 2.4 ± 1.1 | — | — |
| CD19 + CD5 + sTn + | 0.3 ± 0.1 | 29.0 ± 6.3 | — | — |
| CD19 − CD5 + | 52.7 ± 6.6 | 48.5 ± 5.5 | — | — |
| CD19 − CD5 + sTn + | 2.1 ± 0.4 | 30.2 ± 7.1 | — | — |
| CD19 − CD21 + | 1.0 ± 0.1 | 19.3 ± 3.2 | 1.3 ± 0.9 | 15.9 ± 4.1 |
| CD19 − CD21 + sTn + | 0 ± 0.008 | 19.9 ± 4.8 | see FIG. 2 | see FIG. 2 |

Table 2 shows that there are a number of B cell subpopulations which significantly differ in amount in a body fluid comprising peripheral blood of individuals having a pro-tumor immune response as compared to the respective reference value. For example, there is a statistically significant (P value=0.0001) decrease in an amount of overall B cells (e.g., CD19+ cells) in a body fluid comprising peripheral blood of individuals having solid, non-lymphoid tumor and a pro-tumor immune response as compared to the reference value. Additionally, there is a statistically significant (P value<0.0001) increase in an amount of memory B cells (e.g., CD19+ CD21+ cells) in a body fluid comprising peripheral blood of individuals having a pro-tumor immune response as compared to the reference value. There is also a statistically significant (P value<0.0001) increase in the relative percentage of memory B cells hyperexpressing CD21 (e.g., CD19+ CD21++ cells) in peripheral blood of individuals having a pro-tumor immune response as compared to the reference value. As shown in Table 2, the Mean %±SEM for peripheral blood sTn+ memory B cells (e.g., CD19+ CD21+ sTn+ cells) from individuals having solid, non-lymphoid tumor and a pro-tumor immune response is 16.12±3.72; whereas the Mean %±SEM for the reference value is 29.67±5.0. Using 15% as a threshold value of sTn+ memory cells, 75% of the individuals having solid, non-lymphoid tumor and a pro-tumor immune response have a percentage lower than the threshold value. Thus, there is a statistically significant (P value=0.035) decrease in an amount of peripheral blood sTn+ memory B cells in individuals having a pro-tumor immune response as compared to the values in individuals who lack a pro-tumor immune response. There is also a statistically significant (P value<0.0001) increase in an amount of sTn+ B cells (e.g., CD19+ sTn+ cells) in the peripheral blood of individuals having a pro-tumor immune response as compared to the reference value. Additionally, there is also a statistically significant (P value<0.001) increase in an amount of sTn+ B1 cells (e.g., CD19+ CD5+ sTn+ cells) in the peripheral blood of individuals having a pro-tumor immune response as compared to the reference value.

Table 2 shows that there are a number of B cell subpopulations which significantly differ in amount in a sample comprising lymphoid tissue of individuals having a pro-tumor immune response as compared to the respective reference value. For example, there is a statistically significant (P value=0.001) increase in an amount of memory B cells (e.g., CD19+ CD21+ cells) in lymphoid tissues of individuals having a pro-tumor immune response as compared to the reference value. By using a threshold value of 20%, only individuals having a pro-tumor immune response have a percentage of lymphoid tissue CD19+ CD21+ B cells greater than the threshold value. The amount of lymphoid tissue memory B cells could possibly be even greater if only examined was lymphoid tissue which is a foci of a pro-tumor immune response (as opposed to analysis of lymphoid tissue that was picked at random). There is also a statistically significant (P value<0.02) increase in an amount of memory B cells hyperexpressing CD21 (e.g., CD19+ CD21++ cells) in lymphoid tissues in individuals having a pro-tumor immune response as compared to the reference value. Also, there is a statistically significant (P value<0.03) increase in an amount of sTn+ B cells (e.g., CD19+ sTn+ cells) in lymphoid tissue in individuals having a pro-tumor immune response as compared to the reference value.

Table 2 shows that there are a number of follicular dendritic cell subpopulations which significantly differ in amount in a body fluid comprising peripheral blood of individuals having a pro-tumor immune response as compared to the respective reference value. For example, in a body fluid comprising peripheral blood, there is a statistically significant (P value<0.01) increase in an amount of sTn+ FDC (e.g., CD19− CD21+ sTn+ cells) in individuals having a pro-tumor immune response as compared to the reference value; and a statistically significant (P value<0.01) increase in an amount of overall FDC (e.g., CD19− CD21+ cells) in individuals having a pro-tumor immune response as compared to the reference value. Table 2 also shows that there are a number of follicular dendritic cell subpopulations which significantly differ in amount in lymphoid tissue of individuals having a pro-tumor immune response as compared to the respective reference value. For example, there is a statistically significant (P value=0.005) increase in an amount of an overall FDC population (e.g., CD19− CD21+ cells) in individuals having a pro-tumor immune response as compared to the reference value. Using a threshold value of 5% of lymphoid tissue FDC (e.g., CD19− CD21+ cells), only individuals having a pro-tumor immune response have a percentage of lymphoid tissue FDC greater than the threshold value in all samples tested to date (thus, such a threshold value is above all values obtained from healthy controls tested). The amount of lymphoid tissue FDC could possibly be even greater if only examined was lymphoid tissue which is a foci of a pro-tumor immune response (as opposed to analysis of lymphoid tissue that was picked at random).

Using the methods outlined above, an amount of sTn+ FDC (e.g., CD19− CD21+ sTn+ cells) from lymphoid tissue of individuals having a pro-tumor immune response was compared to a reference value. As shown in FIG. 2, such a determination identifies two distinct subpopulations of sTn+ FDC from lymphoid tissue of individuals having solid, non-lymphoid tumor and a pro-tumor immune response ("Cancer"). As shown by FIG. 2, by using a threshold value consisting essentially of a range comprising the reference value from a low of about 35% (threshold value$_{LOW}$) to a high of about 50% (threshold value$_{HIGH}$), 25% of individuals having a pro-tumor immune response have an amount of lymphoid tissue sTn+ FDC greater than threshold value-$_{HIGH}$. While not intending to be bound by theory, these individuals have lymphoid tissues that appear to be highly active foci for a pro-tumor immune response, as evidenced by a predominance of sTn positivity by the FDC. 75% of individuals having a pro-tumor immune response have a percentage of lymphoid tissue CD19− CD21+ sTn+ FDC lower than the threshold value$_{LOW}$. While not intending to be bound by theory, these individuals have lymphoid tissues that appear to represent foci of a pro-tumor immune response against at least one shed tumor antigen other than that containing a terminal sTn.

Table 2 shows that there are a number of T cell subpopulations which significantly differ in amount in a body fluid comprising peripheral blood of individuals having a pro-tumor immune response as compared to the respective reference value. For example, there is a statistically significant (P value<0.001) increase in an amount of sTn+ T cells (e.g., CD19− CD5+ sTn+ cells) in peripheral blood of individuals having a pro-tumor immune response as compared to the reference value.

EXAMPLE 3

This Example further illustrates embodiments of the method according to the present invention for determining an amount of mononuclear cell phenotype in a clinical sample from an individual as an indicator (a diagnostic value, or a prognostic value) related to a pro-tumor immune response. As illustrated in Table 2, an indicator may comprise alterations in amount of mononuclear cell phenotype (altered mononuclear cell phenotype) as determined in clinical samples from individuals having a pro-tumor immune response. As apparent to one skilled in the art from the descriptions herein, such an indicator may be expressed in several ways. For illustrative examples, consider Formula$_I$ and Formula$_{II}$.

Formula$_I$: $(\%tB < T_B)$ and $[(\%mB_{CD19+CD21+} > T_{19+CD21+})$ or $(\%mB_{CD19+CD21++} > T_{19+CD21++})$ or $(\%B_{CD19+sTn+} > T_{19+sTn+})$ or $(\%mB_{CD19+CD21+sTn+} < T_{19+CD21+sTn+})$ or $(\%B_{CD19+CD5+sTn+} > T_{19+CD5+sTn+})$, or $(\%T_{CD19-CD5+sTn+} > T_{19-CD5+sTn+})$ or a combination thereof] = Cancer and PTIR Formula$_{II}$: $(\%mB_{CD19+CD21+} > T_{19+CD21+})$ or $(\%mB_{CD19+CD21++} > T_{19+CD21++})$ or $(\%B_{CD19+sTn+} > T_{19+sTn+})$ or $(\%mB_{CD19+CD21+sTn+} < T_{19+CD21+sTn+})$ or $(\%B_{CD19+CD5+sTn+} > T_{19+CD5+sTn+})$, or $(\%T_{CD19-CD5+sTn+} > T_{19-CD5+sTn+})$ or a combination thereof = PTIR In the above-representative formulas, % tB is an amount of overall number of B cells (e.g., % of CD19+ B cells) in a clinical sample comprising peripheral blood from an individual being screened for a pro-tumor immune response; $T_B$ is equal to a threshold value comprising the minimum amount of overall B cells in peripheral blood of healthy individuals (e.g., Mean−2.5(SEM); or 3.7%); %mB$_{CD19+CD21+}$ is an amount (e.g., %) of memory B cells (e.g., CD19+ CD21+ cells) in a clinical sample comprising peripheral blood from an individual being screened for a pro-tumor immune response; $T_{19+CD21+}$ is equal to a threshold value comprising the maximum amount of memory B cells (e.g., CD19+ CD21+ cells in peripheral blood of healthy individuals (e.g., Mean+2.5(SEM); or 31%); %mB$_{CD19+CD21++}$ is an amount (e.g., %) of CD21 hyperexpressing memory B cells (e.g., CD19+ CD21++ cells) in a clinical sample comprising peripheral blood from an individual being screened for a pro-tumor immune response; $T_{19+CD21++}$ is equal to a threshold value comprising a maximum amount of memory B cells (e.g., CD19+ CD21+30 cells) in peripheral blood of healthy individuals (e.g., Mean+2.5(SEM); or 8.3%); %B$_{CD19+sTn+}$ is an amount (e.g., %) of sTn+ B cells (e.g., CD19+ sTn+ cells) in a clinical sample comprising peripheral blood from an individual being screened for a pro-tumor immune response; $T_{19+sTn+}$ is equal to a threshold value comprising a maximum amount of sTn+ B cells (e.g., CD19+ sTn+ cells) in peripheral blood of healthy individuals (e.g., Mean+2.5(SEM); or 2.3%); %mB$_{CD19+CD21+sTn+}$ is an amount (e.g., %) of sTn+ memory B cells (e.g., CD19+ CD21+ sTn+ cells) in a clinical sample comprising peripheral blood from an individual being screened for a pro-tumor immune response; $T_{19+CD21+sTn+}$ is equal to a threshold value comprising a minimum amount of sTn+ memory B cells (e.g., CD19+ CD21+ sTn+ cells) in peripheral blood of healthy individuals (e.g., Mean−2.5(SEM); or 17.4%); %B$_{CD19+CD5+sTn+}$ is an amount (e.g., %) of sTn+ B1 cells (e.g., CD19+ CD5+ sTn+ cells) in a clinical sample comprising peripheral blood from an individual being screened for a pro-tumor immune response; $T_{19+CD5+sTn+}$ is equal to a threshold value comprising a maximum amount of sTn+ B1 cells (e.g., CD19+ CD5+ sTn+ cells) in peripheral blood of healthy individuals (e.g., Mean+2.5(SEM); or 0.6%); %T$_{CD19-CD5+sTn+}$ is an amount (e.g., %) of sTn+ T cells (e.g., CD19− CD5+ sTn+ cells) in a clinical sample comprising peripheral blood from an individual being screened for a pro-tumor immune response; $T_{19-CD5+sTn+}$ is equal to a threshold value comprising a maximum amount of sTn+ T cells (e.g., CD19− CD5+ sTn+ cells) in peripheral blood of healthy individuals (e.g., Mean+2.5(SEM); or 3.1%); PTIR is an abbreviation for the presence of a pro-tumor immune response; and "Cancer" is indicative of the presence of a solid, non-lymphoid tumor. Thus, using Formula$_I$, a significant difference in an amount of overall B cells combined with a significant difference in any one or more of the memory B cells, sTn+ memory B cells, sTn+ B cells, sTn+ B1 cells, CD21 hyperexpressing memory B cells, and sTn+ T cells, translates into a 99.8% probability that the individual has a pro-tumor immune response and a solid, non-lymphoid tumor. For example, where the individual's peripheral blood has a % of CD19+ B cells less than 3.7%, and where the individual's peripheral blood has an amount of a mononuclear cell subpopulation comprising one or more of: CD19+ CD21+ cells of greater than 31%, CD19+ CD21++ cells of greater than 8.3%, CD19+ sTn+ cells of greater than 2.3%, CD19+ CD5+ sTn+ cells of greater than 0.6%, CD19+ CD21+ sTn+ cells less than 17.4%, and sTn+ T cells of greater than 3.1%, then there is a 99.8% probability that the individual has both a pro-tumor immune response and a solid non-lymphoid tumor. Generally then, Formula$_I$, illustrates the generation of indicators to identify individuals as having or lacking a pathological condition, in providing an additional parameter to a competent health professional in making a medical opinion. Similarly, using the Formula$_{II}$, a significant difference in an amount of mononuclear cell subpopulations designated therein may result in a 99.8% probability that the individual has a pro-tumor immune response. For example, where the individual's peripheral blood has a mononuclear cell subpopulation comprising one or more of: CD19+ CD21+ cells of greater than 31%, CD19+ CD21++ cells of greater than 8.3%, CD19+ sTn+ cells of greater than 2.3%, CD19+ CD5+ sTn+ cells of greater than 0.6%, CD19+ CD21+ sTn+ B cells less than 17.4%, and sTn+ T cells of greater than 3.1%, then there is a 99.8% probability that the individual has a pro-tumor immune response. Generally then, Formula$_{II}$ illustrates the generation of indicators to identify individuals as having or lacking a pathological condition, in providing an additional parameter to a competent health professional in making a medical opinion.

Similarly, and with regard to an indicator related to FDC for purposes of illustration but not limitation, consider Formula$_{III}$.

$$(\%FDC_{CD19-CD21+sTn+} > T_{CD19-CD21+sTn+}) \text{ or } (\%FDC_{CD19-CD21+} > T_{CD19-CD21+}) = \text{P-TIR or P-TIR \& Cancer}$$

wherein $\%FDC_{CD19-CD21+sTn+}$ is an amount (e.g., %) of sTn+ FDC (e.g., CD19– CD21+ sTn+ cells) in a clinical sample comprising peripheral blood from an individual being screened for a pro-tumor immune response; $T_{CD19-CD21+}$ is equal to a threshold value comprising a maximum amount of sTn+ FDC (e.g, CD19– CD21+ sTn+ cells) in peripheral blood of healthy individuals (e.g., Mean–2.5 (SEM); or less than 1%); $\%FDC_{CD19-CD21+}$ is an amount (e.g., %) of FDC (e.g., CD19– CD21+ cells) in a clinical sample comprising lymphoid tissue from an individual being screened for a pro-tumor immune response; and $T_{CD19-CD21+}$ is equal to a threshold value comprising a maximum amount of FDC (e.g., CD19– CD21+ cells) in lymphoid tissue of healthy individuals (e.g., Mean+2.5 (SEM); or about 4%); or $\%FDC_{CD19-CD21+}$ is an amount (e.g., %) of FDC (e.g., CD19– CD21+ cells) in a clinical sample comprising peripheral blood from an individual being screened for a pro-tumor immune response; and $T_{CD19-CD21+}$ is equal to a threshold value comprising a maximum amount of FDC (e.g., CD19– CD21+ cells) in peripheral blood of healthy individuals (e.g., Mean+2.5 (SEM); or about 1.3%). Thus, using the illustrated Formula$_{III}$, a significant difference in any one or more of the measured parameters may translate into a greater than 95% probability that the individual has a pro-tumor immune response, or a pro-tumor immune response and solid, non-lymphoid tumor. For example, and as compared to the control values, where the individual's peripheral blood has a % of CD19– CD21+ sTn+ FDC greater than about 1%, and/or where the individual's lymphoid tissue has a % of CD19– CD21+ FDC greater than 4%, and/or where an individual's peripheral blood has a % of CD19– CD21+ FDC greater than 1.3%, then there is a greater than 99% probability that the individual has either a pro-tumor immune response or both a pro-tumor immune response and a solid non-lymphoid tumor. It will be apparent to one skilled in the art that a mononuclear cell phenotype indicator may combine mononuclear cell subpopulations indicated in Formula$_{III}$ with any one of Formula$_I$ or Formula$_{II}$.

EXAMPLE 4

Figure 3:
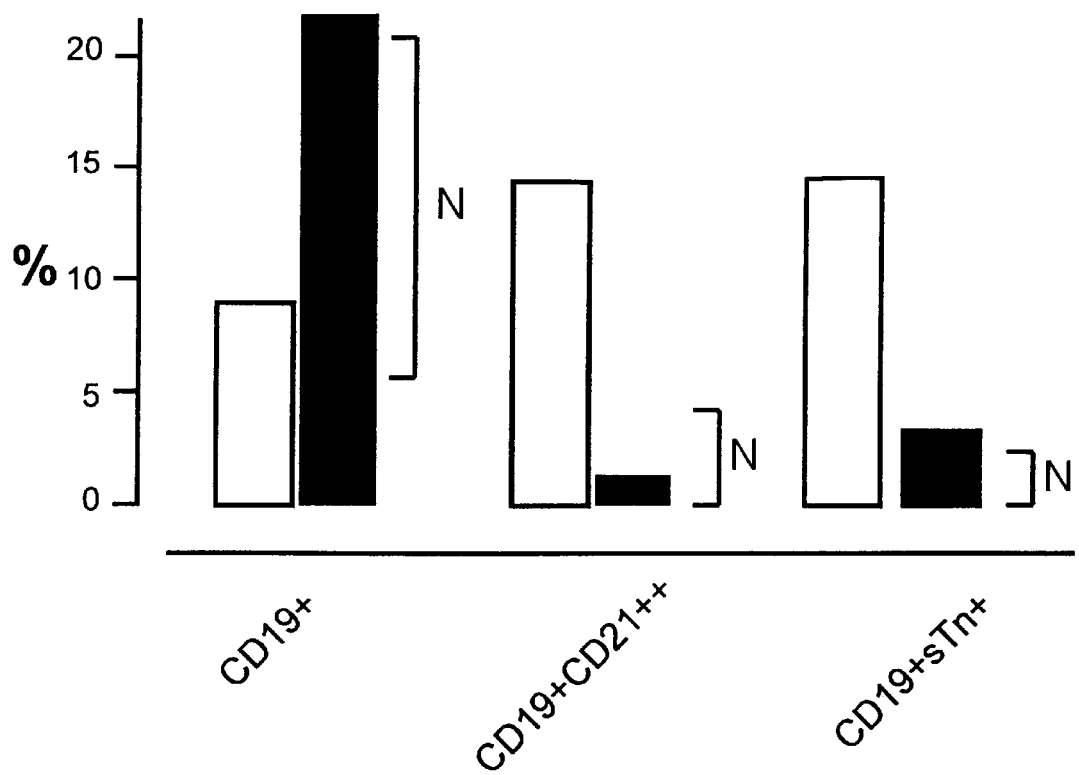
FIG. 3 is a bar graph illustrating amounts of overall B cells (e.g., CD19+ cells), CD21 hyperexpressing memory B cells (e.g., CD19+ CD21++ cells), and sTn+ B cells (e.g., CD19+ sTn+ cells) after surgery but before chemotherapy (□) as compared to the respective amounts after chemotherapy (■), and as compared with normal control values ("]N").

This Example further illustrates an embodiment of the method according to the present invention for determining an amount of mononuclear cell phenotype in a clinical sample from an individual as an indicator (a diagnostic value, or a prognostic value) related to a pro-tumor immune response. Previously described herein in more detail is the use of a prognostic indicator in monitoring anticancer therapy and effects, if any, of the anticancer therapy on any one or more of tumor and a pro-tumor immune response. Essentially, a reference sample from an individual, in which is determined an amount of mononuclear cell phenotype (comprising altered mononuclear cell phenotype) and which was obtained prior to the initiation or before the conclusion of anticancer therapy, is compared to an amount of respective mononuclear cell phenotype determined from a test sample obtained during anticancer therapy but after the time at which the reference sample was obtained, or post anticancer therapy, for any significant differences between the reference sample and the test sample. As an illustration of this embodiment, an individual having a localized colon tumor and a pro-tumor immune response underwent anticancer therapy comprising surgical resection of the tumor followed by multiple regimens of chemotherapeutic treatment. FIG. 3 illustrates a mononuclear cell phenotype comprising an amount of overall B cells (e.g., CD19+ cells), an amount of CD21 hyper-expressing memory B cells (e.g., CD19+ CD21++ cells), and an amount of sTn+ B cells (e.g., CD19+ sTn+ cells) after surgery but before chemotherapy (□) and after chemotherapy (■), and as compared to a reference value established from healthy controls (▯N). Anticancer therapy comprising surgical removal of the tumor resulted in an increase in the amount of overall B cells to within a range observed in the reference value (e.g., 8.7%). As shown in FIG. 3, as a result of three treatments with chemotherapy, the amount of overall B cells remain within the reference values (27%, and after correction for the leukopenia, about 12%). The chemotherapy significantly reduced the amount of CD19+ CD21++ B cells from 14.6% to within a range observed in the reference value (e.g., 1.1%). Likewise, chemotherapy significantly reduced the amount of sTn+ B cells (e.g., CD19+ sTn+ cells) from 14.6% to a level approaching the range of the reference value (e.g., 3.2%). Such an observed effect of anticancer therapy on altered mononuclear cell phenotype associated with tumor and associated with a pro-tumor immune response may be an indicator that the combined anticancer therapy has effected a substantial reduction of tumor burden and is reducing the pro-tumor immune response in the treated individual.

Figure 4:
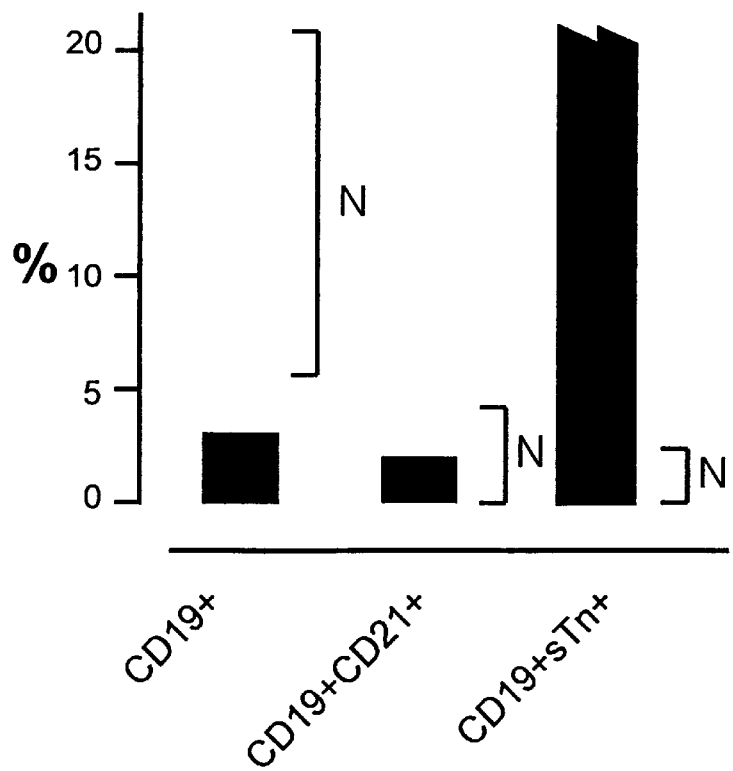
FIG. 4 is a bar graph illustrating amounts of overall B cells (e.g., CD19+ cells), memory B cells (e.g., CD19+ CD21+ cells), and sTn+ B cells (e.g., CD19+ sTn+ cells) after anticancer treatment (■), as compared with normal control values ("]N").
Figure 6:
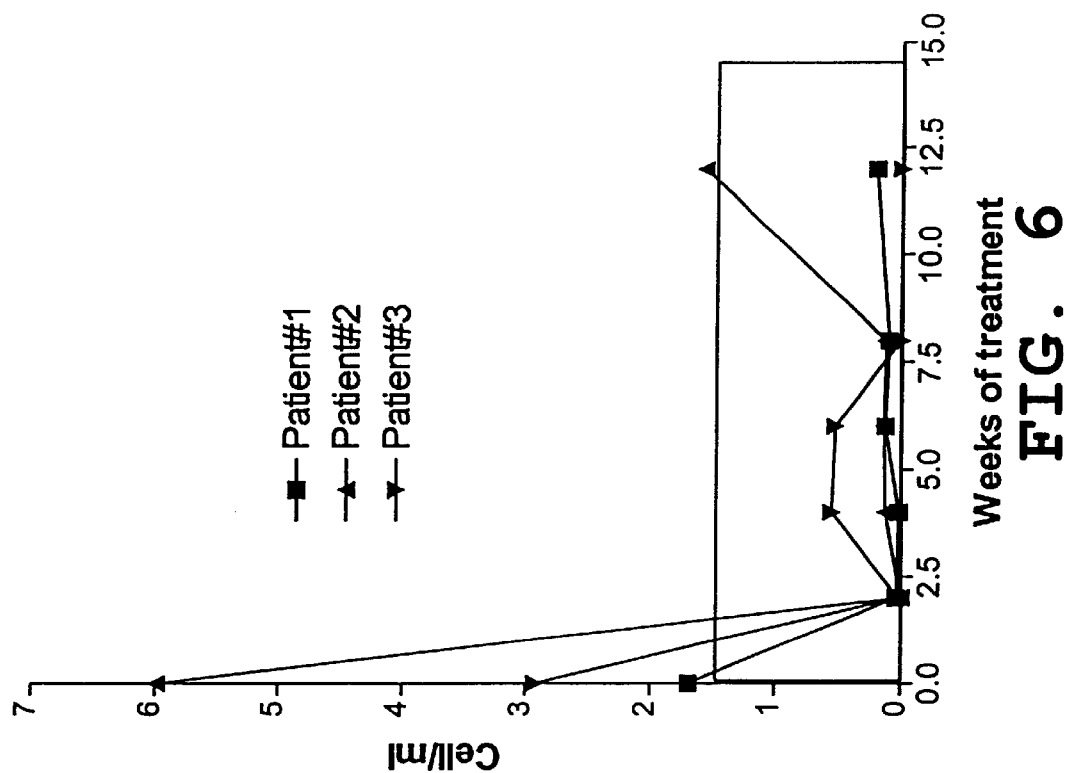
FIG. 6 is a graph showing the depletion of sTn+ B cells (e.g., CD19+ sTn+ cells) effected by anticancer therapy.
Figure 5:
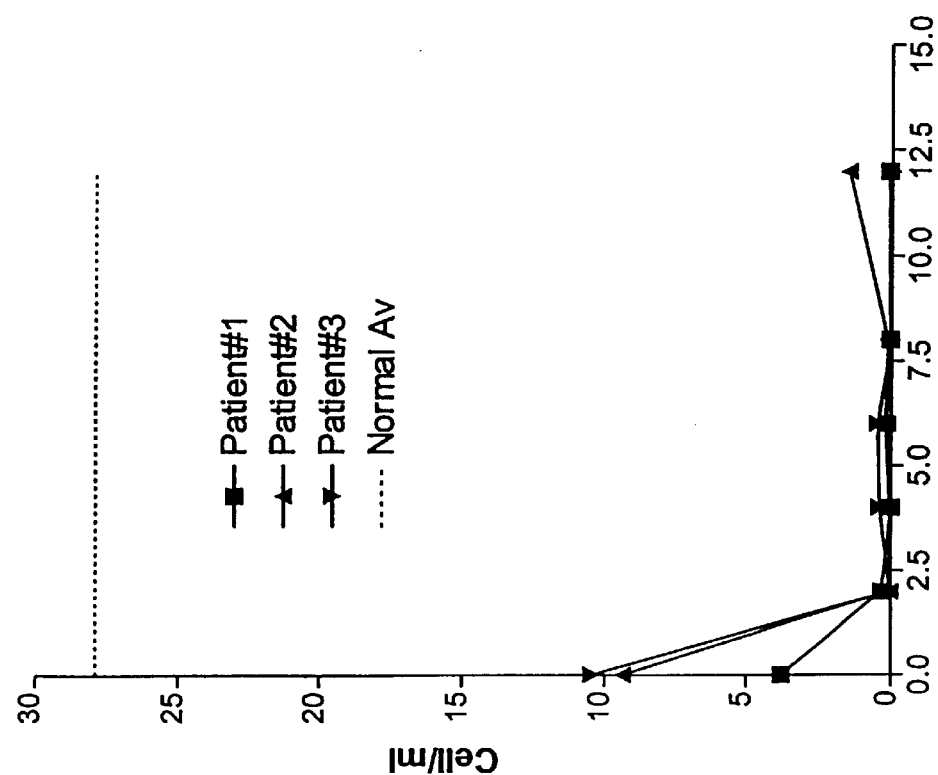
FIG. 5 is a graph showing the depletion of overall B cells (e.g., CD19+ cells) effected by anticancer therapy.

As another illustration of this embodiment, an individual having Stage IV colon cancer with liver metastases and a pro-tumor immune response underwent anticancer therapy comprising surgical resection of the tumor and metastases followed by multiple regimens of chemotherapy. FIG. 4 illustrates a mononuclear cell phenotype comprising an amount of overall B cells (e.g., CD19+ cells), an amount of memory B cells (e.g., as CD19+ CD21+ cells), and sTn+ B cells (e.g., CD19+ sTn+ cells) approximately 1 year after anticancer therapy (■). As shown in FIG. 4, 1 year after anticancer therapy, the amount of overall B cells is below a range observed for the reference value (e.g., 2.9%), an indicator suggestive of residual or recurrent tumor. The amount of memory B cells is a value within a range observed for the reference value (e.g., 2.0%). However, the amount of sTn+ B cells is significantly increased to a level observed in individuals having a pro-tumor immune response (e.g., 46.3%). Together, this mononuclear cell phenotype may comprise an indicator that the individual (a) has a high probability for recurrence and/or has recurrence of tumor, or has residual tumor; and (b) has a pro-tumor immune response. Generally, such indicators provide an additional parameter to a competent health professional in making a medical decision concerning the efficacy of, or need for additional, anticancer therapy.

Figure 8:
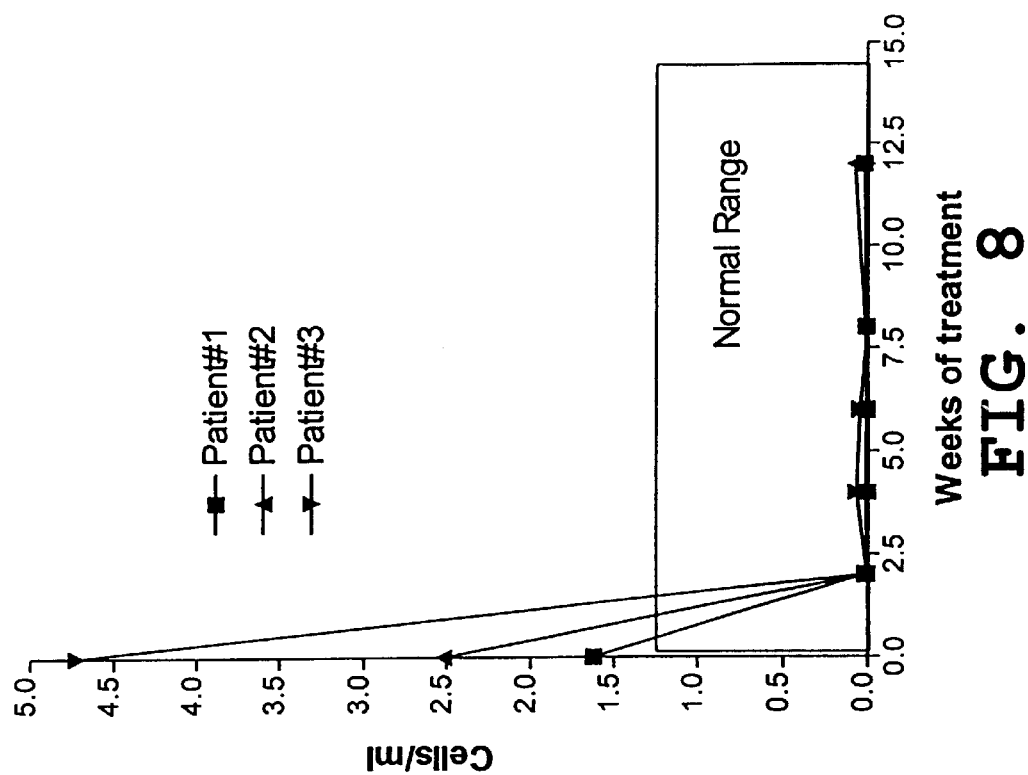
FIG. 8 is a graph showing the depletion of memory B cells (e.g., CD19+ CD21+ cells) effected by anticancer therapy.
Figure 7:
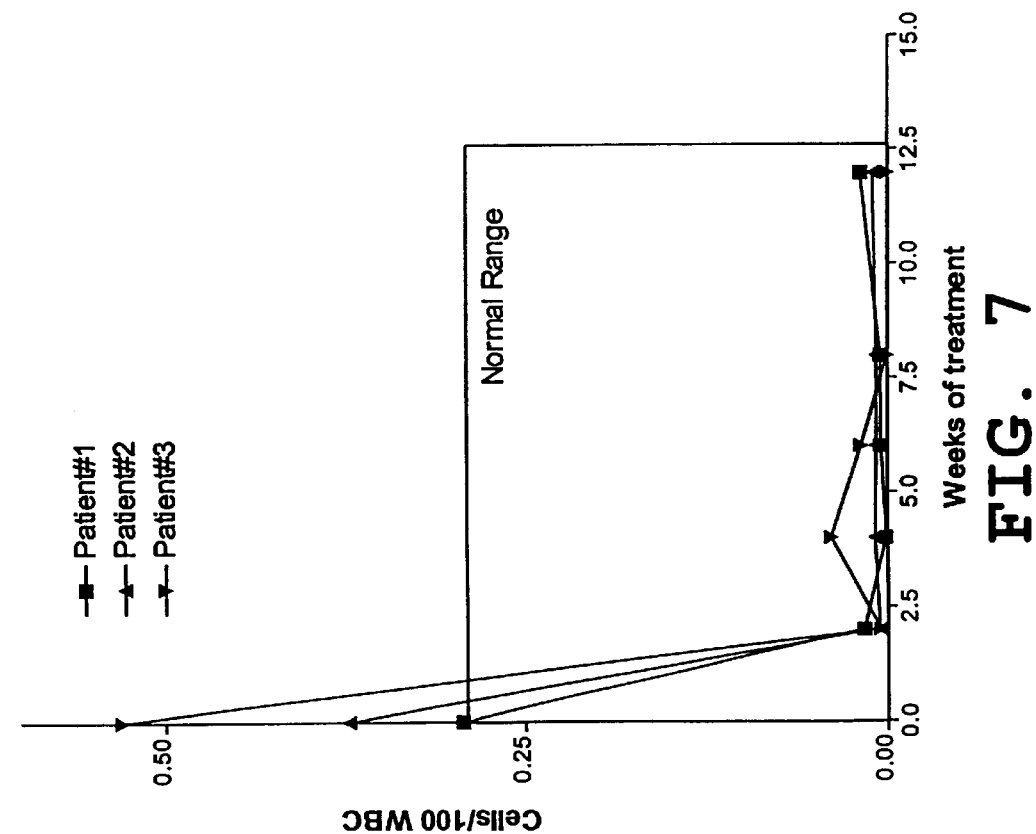
FIG. 7 is a graph showing the depletion of sTn+ memory B cells (e.g., CD19+ CD21+ sTn+ cells) effected by anticancer therapy.

To illustrate another embodiment in which the amount of mononuclear cell phenotype is used as an indicator to monitor efficacy of anticancer therapy, three individuals having a pro-tumor immune response were treated with an immunotherapeutic composition for depleting B cells. The regimen of treatment comprised three administrations of the composition: the initial treatment (week 0), one at week 4, and one at week 8. A reference sample (day 0) was obtained, and test samples were obtained during and after the treatment period, from which peripheral blood samples was determined mononuclear cell phenotype comprising overall B cells (e.g., CD19+ cells), sTn+ B cells (e.g., CD19+ sTn+ cells), memory B cells (e.g., CD19+ CD21+ cells), and sTn+ memory B cells (e.g., CD19+ CD21+ sTn+ cells). As shown in FIGS. 5–8, the anticancer therapy of a pro-tumor immune response (as directed against B cells) of the 3 individuals (■,▲,▼) resulted in a depletion in an amount of overall B cells (FIG. 5), and normalization of the amounts of sTn+ B cells (FIG. 6), sTn+ cells (FIG. 7), and memory B cells (FIG. 8). Thus, the amounts of mononuclear cell phenotype after initiation of treatment, as illustrated in FIGS. 5–8, indicate that the anticancer therapy was effective in reducing the altered mononuclear cell phenotype in peripheral blood of the treated individuals to a mononuclear cell phenotype within the respective reference value.

EXAMPLE 5

This Example illustrates embodiments of assay kits according to the present invention for performing methods for determining an amount of mononuclear cell phenotype comprising one or more mononuclear cell subpopulations in a clinical sample from an individual. As apparent to those skilled in the art, the assay kits may include various components, depending on the complexity of the screening method utilized for determining an amount of at least one mononuclear cell subpopulation comprising mononuclear cell phenotype. An assay kit contains detector molecules that facilitate determination of an amount of mononuclear cell phenotype that may be present in the sample analyzed. In a preferred embodiment, the detector molecules included in the kit according to the present invention comprise at least two detector molecules wherein at least one detector molecule ("first detector molecule") is selected from the group consisting of a detector molecule for detecting a pan B cell marker, a detector molecule for detecting a pan T cell marker, a detector molecule for detecting a pan FDC marker, and a combination thereof; and at least one detector molecule (second detector molecule) for detecting a functional mononuclear cell marker. It will be apparent that the first detector molecule may be used in combination with the second detector molecule for determination of an amount of mononuclear cell phenotype in the sample. The kit may further comprise one or more additional detector molecules that may be used to determine one or more additional mononuclear cell subpopulations comprising mononuclear cell phenotype.

In one preferred embodiment, the kit comprises at least one first detector molecule for detecting a pan lymphocyte marker selected from the group consisting of either a pan B cell marker, a pan T cell marker, and a combination thereof; and a second detector molecule for detecting sTn. For example, in one preferred assay kit, the kit comprises a first detector molecule for detecting a pan B cell marker, wherein the pan B cell marker comprises CD19, and a second detector molecule for detecting sTn; e.g., for determining the amount of overall B cells (e.g., CD19+ cells) and sTn+ B cells (e.g., CD19+ sTn+ cells). In another example, a preferred kit comprises a first detector molecule for detecting a pan T cell cell marker, wherein the pan T cell marker comprises CD3, and a second detector molecule for detecting sTn; e.g., for determining the amount of overall T cells (e.g., CD3+ cells) and sTn+ T cells (e.g., CD3+ sTn+ cells). In another example, a preferred kit comprises a plurality of first detector molecules, wherein one detector molecule is for detecting a pan B cell marker (e.g., CD19) and another detector molecule is for detecting a pan T cell marker (e.g., CD3); and a second detector molecule for detecting sTn. Thus, the kit may be used to determine an amount of overall B cells (e.g., CD19+ cells), an amount of sTn+ B cells (e.g., CD19+ sTn+ cells), an amount of overall T cells (e.g., CD3+ cells), and an amount of sTn+ T cells (e.g., CD3+ sTn+ cells). Alternatively, a preferred kit comprises a plurality of first detector molecules, wherein one detector molecule is for detecting CD19 and another detector molecule is for detecting a CD5; and a second detector molecule for detecting sTn. Thus, the kit may be used to determine an amount of overall B cells (e.g., CD19+ cells), an amount of sTn+ B cells (e.g., CD19+ sTn+ cells), an amount of $B_1$ cells (e.g., CD19+ CD5+ cells), and amount of sTn+ $B_1$ cells (e.g., CD19+ CD5+ sTn+ cells), an amount of overall T cells (e.g., CD5+ CD19− cells), and an amount of sTn+ T cells (e.g., CD5+ CD19− sTn+ cells).

In another preferred embodiment, the assay kit example, the kit comprises a plurality of detector molecules comprising at least one detector molecule for detecting a pan lymphocyte marker, and at least one detector molecule for detecting a functional mononuclear cell marker, and a detector molecule for detecting a pan follicular dendritic cell marker. For example, a preferred kit may comprise a plurality of detector molecules, wherein one detector molecule is for detecting CD19, another detector molecule is for detecting a CD21, and yet another detector molecule is for detecting sTn. Thus, the kit may be used to determine an amount of overall B cells (e.g., CD19+ cells), an amount of sTn+ B cells (e.g., CD19+ sTn+ cells), an amount of memory B cells (e.g., CD19+ CD21+ cells), an amount of sTn+ memory B cells (e.g., CD5+ CD19− sTn+ cells), an amount of CD21 hyper-expressing memory B cells (e.g., CD19+ CD21++ cells), an amount of overall follicular dendritic cells (e.g., CD19– CD21+ cells), and sTn+ follicular dendritic cells (e.g., CD19– CD21+ sTn+ cells). In another example, a preferred kit may comprise a plurality of detector molecules, wherein one detector molecule is for detecting CD19, another detector molecule is for detecting a CD21, and another detector molecule is for detecting sTn, and yet another detector molecule is for detecting CD5. Thus, the kit may be used to determine an amount of overall B cells (e.g., CD19+ cells), an amount of sTn+ B cells (e.g., CD19+ sTn+ cells), an amount of B1 cells (e.g., CD19+ CD5+ cells), an amount of sTn+ B1 cells (e.g., CD19+ CD5+ sTn+ cells), an amount of memory B cells (e.g., CD19+ CD21+ cells), an amount of sTn+ memory B cells (e.g., CD5+ CD19– sTn+ cells), an amount of CD21 hyperexpressing memory B cells (e.g., CD19+ CD21++ cells), an amount of overall T cells (e.g., CD5+ CD19– cells), an amount of sTn+ T cells (e.g., CD5+ CD19– sTn+ cells), an amount of overall follicular dendritic cells (e.g., CD19– CD21+ cells), and sTn+ follicular dendritic cells (e.g., CD19– CD21+ sTn+ cells).

Additionally, an assay kit of each of the above-described embodiments may further comprise an isotype detector molecule for each antibody type of detector molecule used (see, e.g., Example 2 herein for more detail) for determining an amount of mononuclear cell phenotype. In another illustrative example, wherein an aptamer is used as the affinity ligand of the detector molecule, an aptamer of the same general backbone sequence (e.g., differing primarily only in the sequence conferring binding specificity) may be used as an affinity ligand in an isotype detector molecule. In an alternative, one or more of the affinity ligands may lack a detectable label, and a labeled secondary affinity ligand is used to detect the unlabeled affinity ligand when it is bound to the determinant. The assay kit according to the present invention may further comprise one or more controls in any one of the methods in which is determined a mononuclear cell phenotype according to the present invention. For example, a control may comprise an amount of one or more mononuclear cell subpopulations which may be measured using the detector molecules in the assay kit. For example, and depending on the choice of detector molecules included in the assay kit, the control may comprise an amount of one or more mononuclear cell subpopulations selected from the group consisting of overall B cells, sTn+ B cells, memory B cells, sTn+ memory B cells, CD21 hyper-expressing B cells, B1 cells, sTn+ B1 cells, overall T cells, sTn+ T cells, overall follicular dendritic cells, sTn+ follicular dendritic cells. Thus, there may be a separate control for each of mononuclear cell subpopulation comprising mononuclear cell phenotype according to the present invention; or there may be a control for a combination of mononuclear cell subpopulations comprising mononuclear cell phenotype. A control may be stored in a solution, or may be lyophilized for reconstitution, frozen, or a combination thereof. The cells comprising the control may be fixed by prior treatment with any one of a number of solutions known in the art to include, but are not limited to, 1% paraformaldehyde, methanol, methanol/acetone, acetone, 2% (v/v) paraformaldehyde and acetone, and 70% ethanol. Such a control may be used to test the efficacy of one or more detector molecules which may be used to determine an amount of mononuclear cell phenotype in a clinical sample; and may also be reacted with isotype detector molecules as set forth in Example 2 herein. The control may further comprise pre-stained cells, e.g., stained with multiple detector molecules for determining the one or more mononuclear cell subpopulations present in the control. The pre-stained control may be a control for the detection process and instrumentation associated therewith. For example, a pre-stained control may comprise B cells pre-stained with one or more detector molecules comprising a detector molecule for CD19, a detector molecule for sTn, a detector molecule for CD5, and a detector molecule. Pre-stained control cells may be stored in a solution, or may be lyophilized for reconstitution, or may be frozen. Pre-stained control cells may be fixed by prior treatment (either before or after staining) with any one of a number of solutions known in the art.

The assay kit according to the present invention may further comprise one or more standards in a method for determining mononuclear cell phenotype in a clinical sample according to the present invention. A standard may comprise a standard representative of a known amount of one or more mononuclear cell subpopulations which may be measured using the detector molecules in the assay kit. For example, and depending on the choice of detector molecules included in the assay kit, the standard may comprise a known amount of a mononuclear cell subpopulation selected from the group consisting of overall B cells, sTn+ B cells, memory B cells, sTn+ memory B cells, CD21 hyperexpressing B cells, B1 cells, sTn+ B1 cells, sTn+ T cells, follicular dendritic cells, sTn+ follicular dendritic cells, and a combination thereof. Further, a standard: may comprise immortalized cells, and/or a cell line; may comprise unstained cells or stained cells; may be stored in a solution; may be lyophilized for reconstitution; may be frozen; may be fixed by prior treatment with a fixative; or may comprise a combination thereof. A series of standards may comprise a standard that is representative of a threshold value characteristic of an altered mononuclear cell phenotype, and a standard that is representative of a reference value characteristic of a normal range of clinical values as established for the mononuclear cell phenotype (e.g., as established from apparently healthy individuals). For purposes of illustration only, and not limitation, a standard comprising a threshold value for altered mononuclear cell phenotype may be derived from the values illustrated in Table 2 herein (Tumor/PTIR with respect to each mononuclear cell subpopulation), whereas a standard comprising a reference value may be derived from the values illustrated in Table 2 herein (Reference interval, with respect to each mononuclear cell subpopulation) (see also Formula$_I$, Formula$_{II}$, Formula$_{III}$.)

It will be apparent to one skilled in the art that cells useful for controls and standards for the assay kit according to the present invention are readily available. For example, B-cell lines expressing CD19, CD21, and CD22 have been described previously (Randhawa et al., 1997, *In Vitro Cell Dev. Biol. Anim.* 33:803–808); an EBV-positive B cell line ("BEVA") expresses CD19, CD20, and CD21 (de Kroon et al., 1997, *Exp. Hematol.* 25:1062–68), whereas an EBV-positive B cell line ("Jijoye-P3HR-1") strongly expresses CD19 and CD20 with weak expression of CD21 (Yokochi et al., 1988, *Microbiol. Immunol.* 32:957–64); B cell lines expressing CD19, CD20, and CD21 have been described previously (Wagner et al., 1993, *J. Immunol.* 150:4887–99; "YOS-B", Yasukawa et al., 1992, *Br. J. Haematol.* 82:515–21); and CD5+ T cell lines have been described previously (Vassilev et al., 1993, *Clin. Exp. Immunol.*, 92:369–372; and Jurkat cells (sTn+)). For example, an immortalized FDC line expressing Ki-M4 and other surface antigens of human FDC origin have been described previously ("FDC-H1") Orscheschek et al., 1994, *Eur. J. Immunol.* 24:2682–90); EBV-transformed FDC cell lines that share phenotypic and functional characteristics with freshly isolated FDC have been produced (Lindhout et al., 1994, *J.*

*Exp. Med.* 179: 1173–1184); and FDC tumor cells expressing CD21, Ki-M4, R4/23, and other human FDC markers has been described previously (Shek et al., 1996, *Am. J. Surg. Pathol.* 20:313–24).

The kit according to the present invention may further comprise: an isotype detector molecule for isotype of detector molecule included in the kit, one or controls, one or more standards, and a combination thereof. The assay kit may further comprise one or more reagents used in a staining process (e.g., a physiologically acceptable solution/buffer); and/or instructions for use of the assay kit and components; and optionally, other accessories useful in carrying out the methods of the present invention.

As will be apparent to those skilled in the art, the threshold values, and reference values, may vary depending upon such factors which include, but are not limited to, the type of clinical sample analyzed (e.g., origin or tissue type), the nature of the one or more detector molecules used (binding specificity, detectable moiety, etc.), and the process and instrumentation used to detect and quantitate the mononuclear cell phenotype present in the sample. Additionally, it will be apparent to one skilled in the art that the methods of the present invention can also be carried out in conjunction with other diagnostic and prognostic tests in providing more information regarding a pathological condition, if detected.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. An assay kit comprising:

(a) one or more first affinity ligands which specifically bind a determinant selected from the group consisting of a pan B cell marker, a pan follicular dendritic cell (FDC) marker, and a combination thereof; and (b) one or more second affinity ligands which specifically binds a determinant comprising a mononuclear cell marker comprising sialyl-Tn (sTn).

2. The kit according to claim 1, wherein the kit comprises a plurality of different first affinity ligands, one or more of which specifically binds CD19, and one or more of which specifically binds CD5.

3. The kit according to claim 2, wherein the kit further comprises one or more affinity ligands which specifically binds CD21.

4. The kit according to claim 3 further comprising a known amount of reference mononuclear cells for use in comparitively determining alterations in mononuclear cell phenotype in clinical samples.

5. The kit according to claim 2 further comprising a known amount of reference mononuclear cells for use in comparitively determining alterations in mononuclear cell phenotype in clinical samples.

6. The kit according to claim 1, wherein at least one of the affinity ligands of the one or more affinity ligands further comprises a detectable moiety.

7. The kit according to claim 1, further comprising one or more affinity ligands which specifically binds a determinant comprising a pan T cell marker.

8. The kit according to claim 7, wherein at least one of the affinity ligands of the one or more affinity ligands further comprises a detectable moiety.

* * * * *